US008986987B2

(12) United States Patent
Sondermeijer et al.

(10) Patent No.: US 8,986,987 B2
(45) Date of Patent: Mar. 24, 2015

(54) HERPESVIRUS OF TURKEYS VECTORED VACCINE AGAINST AVIAN INFLUENZA IN POULTRY

(75) Inventors: Paulus Jacobus Antonius Sondermeijer, Boxmeer (NL); Iwan Verstegen, Wim de Körverstraat 35 (NL)

(73) Assignee: Intervet Inc., Summit, NJ (US)

(*) Notice: Subject to any disclaimer, the term of this patent is extended or adjusted under 35 U.S.C. 154(b) by 0 days.

(21) Appl. No.: 13/879,822

(22) PCT Filed: Oct. 17, 2011

(86) PCT No.: PCT/EP2011/068073
§ 371 (c)(1),
(2), (4) Date: Apr. 17, 2013

(87) PCT Pub. No.: WO2012/052384
PCT Pub. Date: Apr. 26, 2012

(65) Prior Publication Data

US 2013/0230556 A1 Sep. 5, 2013

Related U.S. Application Data

(60) Provisional application No. 61/407,724, filed on Oct. 28, 2010.

(30) Foreign Application Priority Data

Oct. 18, 2010 (EP) .................................... 10187948

(51) Int. Cl.

| | |
|---|---|
| ***A61K 39/145*** | (2006.01) |
| ***C12N 15/869*** | (2006.01) |
| ***C12N 15/86*** | (2006.01) |
| ***C07K 14/11*** | (2006.01) |
| ***C12N 15/40*** | (2006.01) |
| ***C12N 15/44*** | (2006.01) |
| ***C07K 14/005*** | (2006.01) |
| *A61K 39/00* | (2006.01) |

(52) U.S. Cl.
CPC ............ *A61K 39/145* (2013.01); *C07K 14/005* (2013.01); *C12N 15/86* (2013.01); *C12N 15/869* (2013.01); *A61K 2039/5256* (2013.01); *A61K 2039/552* (2013.01); *C12N 2710/16343* (2013.01); *C12N 2760/16122* (2013.01); *C12N 2760/16134* (2013.01); *C12N 2830/60* (2013.01)
USPC .................. 435/320.1; 424/209.1; 424/93.1; 424/184.1; 424/206.1; 424/199.1; 424/229.1; 435/235.1; 435/91.4; 435/71.1; 435/5

(58) Field of Classification Search
CPC ... A61K 39/12; A61K 39/245; A61K 39/255; C12N 15/86; C12N 2710/16334; C12N 15/869
See application file for complete search history.

(56) References Cited

U.S. PATENT DOCUMENTS

| | | | | |
|---|---|---|---|---|
| 5,187,087 | A * | 2/1993 | Sondermeijer et al. | 435/463 |
| 5,690,939 | A * | 11/1997 | Morgan et al. | 424/229.1 |
| 5,731,188 | A * | 3/1998 | Cochran et al. | 435/235.1 |
| 5,741,696 | A * | 4/1998 | Cochran et al. | 435/235.1 |
| 5,853,733 | A * | 12/1998 | Cochran et al. | 424/199.1 |
| 5,919,461 | A * | 7/1999 | van der Marel et al. | 424/204.1 |
| 5,928,648 | A * | 7/1999 | Cochran | 424/199.1 |
| 5,961,982 | A * | 10/1999 | Cochran | 424/199.1 |
| 6,051,404 | A * | 4/2000 | Morgan et al. | 435/69.3 |
| 6,183,753 | B1 * | 2/2001 | Cochran et al. | 424/199.1 |
| 6,299,882 | B1 * | 10/2001 | Junker | 424/199.1 |
| 6,322,780 | B1 * | 11/2001 | Lee et al. | 424/93.2 |
| 6,913,751 | B2 * | 7/2005 | Cochran et al. | 424/199.1 |
| 7,060,282 | B1 * | 6/2006 | Sondermeijer et al. | 424/229.1 |
| 2002/0081316 | A1 * | 6/2002 | Cochran et al. | 424/199.1 |
| 2002/0085999 | A1 * | 7/2002 | Lee et al. | 424/93.21 |
| 2005/0202045 | A1 * | 9/2005 | Cochran et al. | 424/229.1 |
| 2007/0178115 | A1 * | 8/2007 | Tang et al. | 424/189.1 |
| 2008/0241188 | A1 * | 10/2008 | Esaki et al. | 424/231.1 |
| 2009/0191239 | A1 * | 7/2009 | Wild et al. | 424/205.1 |
| 2010/0189731 | A1 * | 7/2010 | Guo et al. | 424/186.1 |

FOREIGN PATENT DOCUMENTS

| | | | |
|---|---|---|---|
| EP | 0 431 668 | B1 | 6/1991 |
| EP | 431668 | B1 | 6/1991 |

(Continued)

OTHER PUBLICATIONS

Wagner EK, Petroski MD, Pande NT, Lieu PT, Rice M. Analysis of factors influencing kinetics of herpes simplex virus transcription utilizing recombinant virus. Methods. Sep. 1998;16(1):105-16.*
Tarpey I, Davis PJ, Sondermeijer P, van Geffen C, Verstegen I, Schijns VE, Kolodsick J, Sundick R. Expression of chicken interleukin-2 by turkey herpesvirus increases the immune response against Marek's disease virus but fails to increase protection against virulent challenge. Avian Pathol. Feb. 2007;36(1):69-74.*
Pederson NE, Person S, Homa FL. Analysis of the gB promoter of herpes simplex virus type 1: high-level expression requires both an 89-base-pair promoter fragment and a nontranslated leader sequence. J Virol. Oct. 1992;66(10):6226-32.*
Pereira L. Function of glycoprotein B homologues of the family herpesviridae. Infect Agents Dis. Feb. 1994;3(1):9-28.*

(Continued)

*Primary Examiner* — Benjamin P Blumel
*Assistant Examiner* — Rachel Gill

(57) ABSTRACT

The present application applies to the field of veterinary vaccines, in particular of vaccines for poultry against avian influenza. The vaccine is based on a recombinant viral vector expressing the haemagglutinin protein of an influenza virus, wherein the vector is herpes virus of turkeys (HVT) and the haemagglutinin gene is driven by a glycoprotein B gene promoter from a mammalian herpesvirus. A vaccine comprising this HVT+HA vector can be used to induce a protective immune response against avian influenza in poultry, and to reduce the spread of AIV. The invention also relates to methods, uses, and vaccines involving the HVT+HA vector.

9 Claims, 1 Drawing Sheet

(56) References Cited

FOREIGN PATENT DOCUMENTS

| | | | |
|---|---|---|---|
| EP | 0 794 257 | B1 | 9/1997 |
| EP | 0 794 259 | B1 | 9/1997 |
| WO | 01/05988 | A1 | 1/2001 |
| WO | 2007/022151 | A2 | 2/2007 |
| WO | 2009/156367 | A1 | 12/2009 |
| WO | 2010/119112 | A1 | 10/2010 |

OTHER PUBLICATIONS

Cronenberg AM, van Geffen CE, Dorrestein J, Vermeulen AN, Sondermeijer PJ. Vaccination of broilers with HVT expressing an *Eimeria acervulina* antigen improves performance after challenge with Eimeria. Acta Virol. Apr.-Jun. 1999;43(2-3):192-7.*

Takekoshi M, Maeda-Takekoshi F, Ihara S, Sakuma S, Watanabe Y. Use of a glycoprotein gB promoter for expression of genes inserted into the human cytomegalovirus genome. Tokai J Exp Clin Med. Mar. 1998;23(1):39-44.*

Qiu YF, Ge FF, Xu XQ, Chen PY. [Comparison of the relative luciferase activity in secondary CEF by different heterogenous strong promoters, MDV gB promoter and the composed promoters]. Wei Sheng Wu Xue Bao. Apr. 2006;46(2):314-7. Chinese.*

Lan D, Shi X, Wang Y, Liu C, Wang M, Cui H, Tian G, Li J, Tong G. [Construction of a recombinant HVT virus expressing the HA gene of avian influenza virus H5N1 via Rde/ET recombination system]. Wei Sheng Wu Xue Bao. Jan. 2009;49(1):78-84. Chinese.*

Pharmingen, Inc. "Baculovirus expression vector system". Instruction manual, 6th Ed. May 1999.*

Hengartner,C.J., Klupp,B.G., Mettenleiter,T.C. and Enquist,L.W. TPA_exp: Suid herpesvirus 1, complete genome. NCBI GenBank Acc. No. BK001744. Dec. 20, 2003.*

Ceva, Contributions, Oct. 3, 2010. http://www.ceva.com/en/Responsibility/Contributions. Retrieved via https://webarchive.org.*

Baigent et al., "Herpesvirus of turkey reconstituted from bacterial artificial chromosome clones induces protection against Marek's disease", Journal of General Virology, 2006, pp. 769-776, vol. 87.

Brun et al., "Antigen delivery systems for veterinary vaccine development Viral-vector based delivery systems", Vaccine, 2008, pp. 6508-6528, vol. 26.

Cox et al., Non-Lethal Viral Challenge of Influenza Haemagglutinin and Nucleoprotein DNA Vaccinated Mice Results in Reduced Viral Replication, Scandinavian Journal of Immunology, 2002, pp. 14-23, vol. 55.

Cronenberg et al., "Vaccination of broilers with HVT expressing an *Eimeria acervulina* antigen improves performance after challenge with *Eimeria*", Acta Virology, Apr.-Jun. 1999, pp. 192-197, vol. 43(2-3), Abstract, PubMed-NCBI, http://www.ncbi.nlm.nih.gov/pubmed/10696444, Apr. 12, 2013.

Cui et al., "Construction of an infectious Marek's disease virus bacterial artificial chromosome and characterization of protection induced in chickens", Journal of Virological Methods, 2009, pp. 66-72, vol. 156.

Dartiel et al., "Herpesvirus of Turkey Recombinant Viruses Expressing Infectious Bursal Disease Virus (IBDV) VP2 Immunogen induce Protection against an IBDV Virulent Challenge in Chickens", Virology, 1995, pp. 481-490, vol. 211.

Luschow et al., "Protection of chickens from lethal avian influenza A virus infection by live-virus vaccination with infectious laryngotracheitis virus recombinants expressing the hemagglutinin (H5) gene", Vaccine, 2001, pp. 4249-4259, vol. 19.

Pederson et al., "Analysis of the gB Promoter of Herpes Simplex Virus Type 1: High-Level Expression Requires both an 89-Base-Pair Promoter Fragment and a Nontranslated Leader Sequence", Journal of Virology, 1992, pp. 6226-6232, vol. 66(10).

Pereira L., "Function of glycoprotein B homologues of the family herpesviridae", Infect. Agents Dis., 1994, pp. 9-28, vol. 3(1), Abstract, PubMed-NCBI, http://www.ncbi.nlm.nih.gov/pubmed/7952927, Apr. 12, 2013.

Sondermeijer et al., "Avian herpesvirus as a live viral vector for the expression of heterologous antigens", Vaccine, 1993, pp. 349-358, vol. 11(3).

Sonoda et al., "Development of an Effective Polyvalent Vaccine against both Marek's and Newcastle Diseases Based on Recombinant Marek's Disease Virus Type 1 in Commercial Chickens with Maternal Antibodies", Journal of Virology, 2000, pp. 3217-3226, vol. 74(7).

Swayne et al., "Protection against diverse highly pathogenic H5 avian influenza viruses in chickens immunized with a recombinant fowlpox vaccine containing an H5 avian influenza hemagglutinin gene insert", Vaccine, 2000, pp. 1088-1095, vol. 18.

Swayne, David E., Avian influenza vaccines and therapies for poultry, Comparative Immunology, Microbiology and Infectious Diseases, 2009, pp. 351-363, vol. 32.

Takekoshi et al., "Use of glycoprotein gB promoter for expression of genes inserted into the human cytomegalovirus genome", Tokai J. Exp. Clin. Med., Mar. 1998, pp. 39-44, vol. 23(1), Abstract, PubMed-NCBI, http://www.ncbi.nlm.nih.gov/pubmed/9972535, Apr. 12, 2013.

Tarpey et al., "A recombinant turkey herpesvirus expressing chicken interleukin-2 increases the protection provided by in ovo vaccination with infectious bursal disease and infectious bronchitis virus", Vaccine, 2007, pp. 8529-8535, vol. 25.

Veits et al., "Newcastle disease virus expression H5 hemagglutinin gene protects chickens against Newcastle disease and avian influenza", Proceedings of the National Academy of Sciences U.S.A., May 23, 2006, pp. 8197-8202, vol. 103(21).

Walsh et al., "Recombinant Rinderpest Vaccines Expressing Membrane-Anchored Proteins as Genetic Markers: Evidence of Exclusion of Marker Protein from the Virus Envelope", Journal of Virology, Nov. 2000, pp. 10165-10175, vol. 74(21).

Zhou et al., "Protection of chickens with or without maternal antibodies, against IBDV infection by a recombinant IBDV-VP2 protein", Vaccine, 2010, pp. 3990-3996, vol. 28.

The 5th International Workshp on the Molecular Path Virus & 1st Symposium on Avian Herpesviruses, http://www.georgiacenter.uga.edu/cch/register/5th-international-workshop-molecular..., Oct. 14, 2010.

International Search Report for corresponding PCT/EP2011/068073, mailed on Jan. 16, 2012.

Ceva, Contributions, 2010, website.

Okazaki, W. et al., Protection against marek's disease by vaccination with a herpesvirus of turkeys, Avian Diseases, 1970, pp. 413-429, vol. 14, No. 2.

The University of Georgia Center, The 5th international workshop on the molecular path virus & 1st symposium on avian herpesviruses, www.georgiacenter.uga.edu/cch/register/5th-international-workhop-molecular . . . , Oct. 10, 2010, 1-2.

* cited by examiner

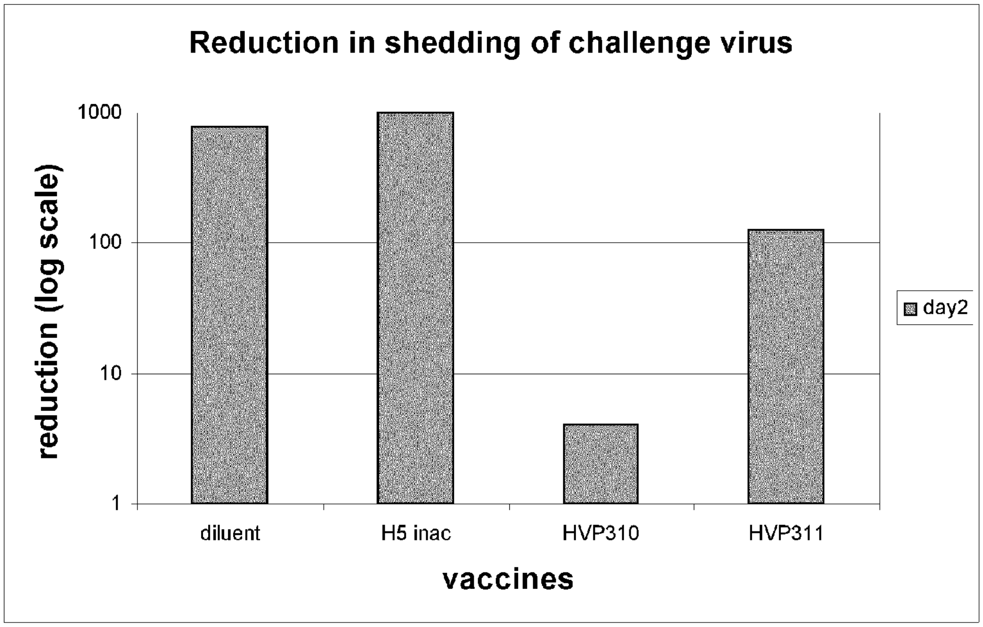
Reduction in shedding of challenge virus
reduction (log scale)
1000
100
10
1
diluent
H5 inac
HVP310
HVP311
vaccines
day2

HERPESVIRUS OF TURKEYS VECTORED VACCINE AGAINST AVIAN INFLUENZA IN POULTRY

CROSS-REFERENCE TO RELATED APPLICATIONS

This application is a national stage entry under 35 U.S.C. §371 of PCT/EP2011/068073, filed on Oct. 17, 2011, which claims priority to U.S. Provisional Application No. 61/407,724, filed on Oct. 28, 2010, and EP Application No. 10187948.4, filed on Oct. 18, 2010. The content of PCT/EP2011/068073 is hereby incorporated by reference in its entirety.

The present application applies to the field of veterinary vaccines, in particular of vaccines for poultry against avian influenza. The vaccine is based on a recombinant viral vector expressing the haemagglutinin protein of an influenza virus, wherein the vector is herpes virus of turkeys (HVT) and the haemagglutinin gene is driven by a glycoprotein B gene promoter from a mammalian herpesvirus. A vaccine comprising this HVT+HA vector can be used to induce a protective immune response against avian influenza in poultry, and to reduce the spread of AIV. The invention also relates to methods, uses, and vaccines involving the HVT+HA vector.

Herpes virus of turkeys (HVT) was described around 1970 as a herpesvirus infecting turkeys, and having antigenic features in common with Marek's disease virus (MDV). Whereas MDV is highly pathogenic for chickens, HVT is apathogenic to chickens and could be used for effective vaccination against infection and disease caused by MDV (Okazaki et al., 1970, Avian Diseases, vol. 14, p. 413-429). Since then, vaccination of chickens against MDV by using HVT has become part of the standard vaccination program of billions of chickens produced worldwide every year. Very helpful in this regard was the finding that HVT, unlike MDV, can be purified from the host cells in which it was produced, e.g. by sonication, and can be marketed as a freeze-dried stable vaccine.

HVT replicates in the birds' lymphocytes, in particular in the peripheral blood lymphocytes (PBL's), consequently it is a systemic virus. It induces an immune response of long duration, which is mostly aimed at the cellular-, not at the humoral immune system.

HVT vaccines can be applied to chickens at an early age, which is a combined result of HVT's apathogenic nature, as well as its relative insensitiveness to maternally derived antibodies against MDV or HVT. Consequently, HVT vaccines can be inoculated into chicks either at the day of their hatching from the egg (day one), or even before hatching, while still in the egg. This last approach, in ovo vaccination, is commonly applied at day 18 of embryonic development (ED), which is about 3 days before hatch.

HVT is currently classified in the subfamily of alphaherpesvirinae, and is also known as: Meleagrid herpesvirus 1, turkey herpesvirus, or Marek's disease virus serotype 3.

The HVT virion has all the features of a typical herpesvirus, and is about 160 nm in size in its enveloped form. Within the capsid it comprises a large genome of linear double stranded DNA. The complete sequence of about 159 kb viral genome is known since 2001 (Genbank accession nr. AF291866).

However, long before this, the HVT genome had been studied and manipulated; particularly its apathogenic properties have lead to research into the use of HVT as a viral vector for expression and delivery of various proteins to a host chicken that was inoculated with the HVT recombinant. Examples are the expression of genes coding for antigens from other poultry pathogens such as: infectious bursal disease virus (IBDV) (Darteil et al., 1995, Virology, vol. 211, p. 481-490), and Newcastle disease virus (NDV) (Sondermeijer et al., 1993, Vaccine, vol. 11, p. 349-358). But also the expression has been described of a parasite antigen (Cronenberg et al., 1999, Acta Virol., vol. 43, p. 192-197), or of a cytokine, to manipulate the chicken's immune response (WO 2009/156,367; Tarpey et al., 2007, Vaccine, vol. 25, p. 8529-8535).

Many locations for insertion of the heterologous gene into the HVT genome in suitable non-essential loci have been investigated, e.g. in the unique short region of the HVT genome (EP 431,668); or in the unique long region (EP 794,257).

Several methods have been described for inserting heterologous nucleic acids into HVT: using homologous recombination (Sondermeijer et al., supra), cosmid regeneration (U.S. Pat. No. 5,961,982), or Bacmids (bacterial artificial chromosomes) (Baigent et al., 2006, J. of Gen. Virol., vol. 87, p. 769-776).

For large scale production HVT is commonly produced in vitro, in cultures of chicken embryo fibroblast cells (CEF's). These are primary cells prepared by trypsinisation of chicken embryos. The CEF's are plated in monolayers and infected with the HVT. This then replicates in these fibroblast cells, even though in vivo HVT replicates in lymphoid cells.

Currently a number of commercial vaccine products are available that comprise an HVT vector expressing a heterologous antigen. For instance: the NDV F-antigen: Innovax®-ND-SB (MSD Animal Health), and Vectormune® HVT-NDV (Ceva); the IBDV VP2 antigen: Vaxxitek® HVT+IBD (Merial), and Vectormune® HVT-IBD (Ceva); or antigens from infectious laryngo-tracheitis virus: Innovax®-ILT (MSD Animal Health).

The application of such HVT vector vaccines to poultry will generate an immune response against the expressed heterologous gene, as well as against HVT/MDV. Because the virulence of MDV field strains has increased over time, a typical vaccination against MDV these days incorporates a further MDV vaccine component in addition to the HVT virus or vector, such as an MDV serotype 1 or 2 vaccine strain, e.g. an MDV Rispens or MDV SB1 strain respectively.

Influenzavirus (IV) is an orthomyxovirus that is infectious to many species of hosts. From the influenza particle itself it is not entirely possible to determine which host type it has infected, or will infect in future. Therefore, in practice, an influenzavirus which can infect and replicate a certain species is commonly referred to as belonging to that species, although cross-infections to other species do regularly occur, for instance: from waterfowl to chickens; from chickens to swine, cats, or humans; from humans to horses, etc. Consequently, avian influenza virus (AIV) relates to the virus that can infect avians. The AIV can cause the disease: Avian influenza (AI), which is also known as 'fowl plague', or 'bird flu', and is a notifiable disease in many countries. Depending on the patho-type of the infecting AIV and the immune status of the infected birds, the disease can vary from a subclinical, to a mild respiratory, to a highly lethal outcome.

Avian influenza in commercial poultry is routinely countered by vaccination in those areas of the world where AIV is endemic, e.g. in Asia and the Middle East. In other areas, such as Europe and North-America, vaccination is government-regulated and allowed only in cases of outbreaks, and in combination with quarantine- and eradication measures.

Of special concern are the so-called highly pathogenic (HP) type AIV viruses, as they pose important zoonotic risks of spread from birds to other species, including humans. The HP AIV possess an HA protein which contains a number of basic amino acids at the cleavage site of the HA1 and HA2 parts of the HA protein. The presence of these basic amino acids makes that the HA protein activation by cleavage can be done by a proteases that occur also in organs other than the respiratory tract where low pathogenic AIV replicate. This results in the more systemic viraemia and the severity of HP AIV infection.

An influenza A type virion, such as AIV, comprises a genome consisting of single stranded RNA of negative polarity, divided into 8 segments, encoding 10 proteins. The viral proteins most relevant for immunological purposes are the haemagglutinin (HA) and neuraminidase (N). The HA is the main antigen, which can induce a protective humoral immune response. AIV are classified by the serotype variant of their HA and N proteins: H1-H16 and N1-N9 have so far been described. HP AIV are always of the H5 or H7 subtype.

Even though an influenza particle is not limited to infecting a specific species, there does seem to be a prevalence of certain IV serotypes in certain species: IV serotypes H1 and H3 in pigs; H3 and H7 in horse; H3 in dogs; H5 in cats; H 7 and H9 in turkeys; and H5, H7, and H9 in chickens.

Because an immune response against influenza is serotype specific, vaccines against influenza generally match the immunological subtype of the IV circulating in the field. Commercial AI vaccines comprise whole inactivated AIV in an oil-adjuvanted emulsion, or a live attenuated AIV vaccine strain.

Nevertheless, changes in the IV field-virus over time, known as 'genetic drift' occur. In practice, an IV strain that differs from existing strains by more than 90% in the amino acid sequence identity of its HA protein will be designated as a new antigenic class, and will get a new 'clade' number. This phenomenon can confront a target population with an IV that has more or less changed its immunological profile since the last infection or vaccination. This can make existing vaccines, even when of the correct subtype, less effective over time, thus requiring an update of the vaccine virus. Among other reasons, influenza vaccines based on recombinant DNA techniques have been developed to facilitate such an update. For instance a vaccine of an IV-HA subunit that is expressed via the baculovirus expression vector system. By way of routine molecular biological techniques, the expressed H5 HA gene can be exchanged for a more recent one, when required.

Similarly, vector vaccines for AI have been developed that express an HA protein in the context of a live carrier microorganism. Examples of such vectors are viruses such as: infectious laryngotracheitis virus (ILTV) (Lüschow et al., 2001, Vaccine, vol. 19, p. 4249-59); Rinderpest virus (Walsh et al., 2000, J. Virol., vol. 74, p. 10165-10175); vesicular stomatitis virus (Roberts et al., 1998, J. Virol., vol. 247, p. 4704-4711); fowl pox virus (Swayne et al., 2000, Vaccine, vol. 18, p. 1088-1095); Adenovirus (Toro et al., 2010, Avian Diseases, vol. 54, p. 224-231); and NDV (Veits et al., 2006, PNAS USA, vol. 103, p. 8197-8202).

Of these, the fowl pox vector based Trovac® AIV-H5 vaccine (Merial), is commercially available.

An AI vaccine for poultry is of course intended to protect the vaccinated animal against symptoms of avian influenza, and against re-infection in the future. However, almost equally relevant for a viral disease with zoonotic and pandemic potential like AIV, is the capability of the vaccine to reduce the spread of the wild type virus in the environment, e.g. to other flocks, to migratory or indigenous wild birds, or to other animal species. Reduction of virus spreading can be obtained by inducing a very efficient immune response in the vaccinated bird.

AI vaccines that are subunit- or vector vaccines have the advantage that they can be applied in a DIVA approach: "differentiation of infected and vaccinated animals", also known as: 'marker vaccines'. This applies because the recombinant vaccines only induce antibodies against the expressed viral protein, not to other viral proteins as would occur in the case of infection with a whole virus. DIVA is important for those countries or economic sectors that want to maintain and certify an AIV-free status e.g. for export purposes.

The current vaccines that are based on whole inactivated AIV in an adjuvanted oil-emulsion do not allow the distinction by DIVA. In a worst case scenario, poultry vaccinated with such vaccines will carry a broad spectrum of antibodies against AIV, but if these are not completely protective, the birds could still be carriers of live infectious AIV, although that would go unnoticed.

A live recombinant viral vector for the expression and delivery of a heterologous antigen must be able to overcome a number of biological stresses upon its stability and efficacy: first the capability to generate progeny after transfection. This indicates the recombinant virus is viable. Next, the capability to replicate in vitro in a host cell-line for many cycles while maintaining expression of the heterologous gene. This indicates the recombinant was not attenuated by the insertion, and the insert is stably replicated and expressed. Then, replication and expression in vivo. This indicates the recombinant can overcome the significant selection pressure in a live animal, such as posed by the immune system. Generally, the loss of expression of the foreign gene favours a faster replication in the animal; such 'escape mutants' have acquired mutations, or major deletions in the foreign gene, and they overgrow the intact vectors. Finally, the replication in the animal needs to be able to generate such an effective immune response that the inoculated animal is protected.

Of special concern in regard to the efficacy in vivo, is the behaviour of the viral vector vaccine in animals that already possess antibodies; against the vector and/or the heterologous gene it expresses. For young animals these antibodies are mostly derived from their mothers who had been thoroughly vaccinated against common pathogens; hence their designation as maternally derived antibodies (MDA). Such antibodies can disturb the replication of the vector and/or the expression of the foreign gene, because they can stimulate the animals' immune system to (unintended) clearance of the vector vaccine.

Recombinant viral vector constructs of an HVT vector with an IV-HA gene insert have been described: the company CEVA has announced a "VECTORMUNE HVT-AI" product on an internet website (http_www_ceva_com/en/Responsibility/Contributions), but no details are available yet.

Lan et al. (2009, Acta Microbiologica Sinica, vol. 49, p. 78-84) describe an HVT vector with an H5 IV-HA gene insert, generated by using an improved technique of Bacmid recombination. Both from a translation of this paper (which is in Chinese), and from a corresponding paper on the recombination technology that was used for MDV (Cui et al., 2009, J. of Virol. Meth., vol. 156, p. 66-72), it is apparent that Lan et al. constructed their recombinant HVT by insertion of an expression cassette into the Us2 gene of HVT; the expression cassette contained an IV H5 HA gene under the control of the human cytomegalovirus immediate early gene (IE-hCMV) promoter. The cassette contains additional elements needed for the cloning and selection process. The paper by Lan et al. only describes the cloning and rescue of an HVT+H5 recombinant; no animal testing is reported, nor any efficacy or stability data from tests in vitro or in vivo.

Alternatively, Zhou et al. (2010, Vaccine, vol. 28, p. 3990-3996), mentions the use of a gB promoter for the expression of IBDV VP2, from the Us10 locus of MDV1. Remarkably this feature is briefly mentioned in the abstract, but the rest of the paper describes the construction and use of an MDV1 vector which expresses lacZ and VP2 driven by the hCMV-IE promoter from the Us2 locus ?

Sonoda et al. (2000, J. of Virol., vol. 74, p. 3217-3226) describe the use of an MDV1 gB gene promoter to drive the expression of an NDV F gene, from the Us10 locus of MDV1.

Takekoshi et al. (1998, Tokai J. Exp. Clin. Med., vol. 23, p. 39-44) describe the use of the gB gene promoter from hCMV for expression of heterologous genes in hCMV.

US2008/0241188 describes the use of the CMV IE gene promoter to drive an AIV HA gene in an HVT vector.

WO2007/022151 describes the use of the hCMV early gene promoter to drive an AIV HA gene in a human adenovirus vector.

WO01/05988 describes the use of the mCMV IE gene promoter and the SV40 promoter to drive genes from avian leokosis virus, in an HVT vector.

Sonoda et al. (J. of Virol., vol. 74, p. 3217) describe the use of the MDV1 gB gene promoter to drive the NDV F gene in an MDV1 vector.

WO2010/119112 describes (in examples 23-25) the use of a CMV IE gene promoter to drive the expression of an H5 type HA gene from AIV in the context of an HVT vector.

It is an object of the present invention to generate an AI vaccine based on an HVT vector; the vector vaccine should induce an effective immune protection against infection and disease caused by AIV in poultry.

The main requirement for such an immunologically and economically feasible vector vaccine product are that it is stable, both in replication of the vector and in the expression of the inserted heterologous gene. This combination allows for the extensive rounds of replication in vitro that are necessary for large scale production, as well as the continued expression and presentation to the host's immune system of the inserted foreign gene, when the vector vaccine is replicating in an inoculated host animal. In addition, this stability will allow the vector vaccine to comply with the very high standards of safety and biological stability that must be met by a recombinant virus that is to be introduced into the field, in order to obtain a marketing authorisation from national governmental authorities.

The inventors were surprised to find that the promoters that had been used in the prior art to drive the expression of heterologous genes in HVT, could not be used for the expression of an IV HA gene in the context of an HVT vector.

Several promoters were tested: a Rous Sarcoma virus-long terminal repeat (RSV LTR) promoter (as described in EP 431,668: derived pRSVcat (Gorman et al., 1982, PNAS USA, vol. 79, p. 6777-6781)); and an hCMV IE gene promoter (derived from pl17: Cox et al., 2002, Scand. J. Immunol., vol. 55, p. 14-23), to drive the expression of an IV H5 HA gene, in the Us10 locus of the HVT genome. The vector with the hCMV IE promoter did yield plaques after transfection, however these could not be amplified for a number of rounds; the HVT vector with LTR promoter did produce plaques that could be amplified, however these only showed very weak HA expression, and when tested in animals as recombinant virus HVP142, did not provide a significant protective effect within 2-3 weeks (see the Examples).

In this situation, it was totally unexpected that a gB gene promoter from a mammalian herpesvirus, which had not been described before for driving heterologous gene-expression in HVT, nor for the expression of an IV HA gene, could be used to construct an HVT vector vaccine expressing an IV HA gene insert, which advantageously showed stability in vector replication and immunological effectiveness in foreign gene expression.

Without wishing to be bound by theory, the inventors speculate that the gB gene promoter from a mammalian herpesvirus, when used for the expression of an IV HA gene in the context of an HVT vector, provides just the right balance between the strength of expression of the heterologous gene, and the strain this puts on the replicative capacity of the recombinant HVT.

Therefore, the invention relates to an HVT vector comprising a heterologous nucleic acid which comprises a nucleotide sequence capable of encoding an IV HA protein, characterised in that said nucleotide sequence is operatively linked to a glycoprotein B (gB) gene promoter from a mammalian herpesvirus.

The HVT vector according to the invention is stable in replication, and provides a sustained expression of the inserted IV HA gene, both in vitro and in vivo. The HVT+HA vector, when used in a vaccine for poultry, induced a strong immune response that could protect birds against disease caused by a severe AIV challenge infection, and could significantly reduce the spread of the challenge virus to the environment.

A "vector" for the invention is a live recombinant carrier micro-organism, here: an HVT.

A "heterologous nucleic acid" for the invention, is a nucleic acid that did not occur in the parental HVT that was used to generate the recombinant HVT vector according to the invention.

A "protein" for the invention is a molecular chain of amino acids. The protein can, if required, be modified in vivo or in vitro, by, e.g. glycosylation, amidation, carboxylation, phosphorylation, pegylation, or changes in spatial folding. A protein can be of biologic or of synthetic origin. The protein can be a native or a mature protein, a pre- or pro-protein, or a functional fragment of a protein. Inter alia, immunologically active peptides, oligopeptides and polypeptides are included within the definition of protein.

A "promoter" is well known to be a functional region on the genome of an organism that directs the transcription of a downstream coding region. A promoter thus is a DNA fragment, that is situated upstream, i.e. to the 5' side, of an open reading frame, typically a gene.

As is well known, a promoter initiates mRNA synthesis of the gene it controls, starting from the 'transcription start site' (TSS). The mRNA produced is in turn translated into protein starting from the gene's startcodon, which is the first ATG sequence in the open reading frame (the first AUG in the mRNA). Typically the TSS is located at 30-40 nucleotides upstream of the start codon. A TSS can be determined by sequencing the 5' end of the mRNA of a gene, e.g. by the RACE technique.

A promoter does not have a specific length, however in general promoters are comprised within 1000 nucleotides upstream of the position of the A of the startcodon, which is generally indicted as A+1; most promoters are situated between −500 and A+1, typically between nucleotides −250 and A+1.

Also, promoters do not have a fixed nucleotide sequence, but they do contain a number of recognisable, conserved sequence elements; these elements are involved in binding transcription factors, and directing the RNA polymerase, but also in the regulation of the time, the duration, the conditions, and the level of transcription that is to follow. This way the promoter is responsive to signals from regulatory elements such as enhancers, or to DNA binding factors such as drugs, hormones, metabolites, etc. A well known conserved promoter element is the TATA box, typically situated within the 50 nucleotides upstream of the TSS, usually about 30 nt upstream from the TSS. Other examples of conserved promoter elements are the CAAT box, typically at about 75 nt upstream from the TSS, and the GC box typically at about 90 nt upstream from the TSS.

The location and size of a promoter can conveniently be determined using standard tests, such as the expression of a marker gene by subcloned smaller or larger sections of a suspected promoter. In a similar way, by testing the expression of a marker gene (by detecting RNA or protein production), the relative strength of different promoters can be determined and compared.

In practice a promoter can simply be selected by subcloning the region in between two consecutive genes, e.g. from the poly A signal of the upstream gene to the TSS of the downstream gene, followed by trimming of the cloned area when appropriate.

Because a promoter is adjacent to the gene of which it controls the expression in the native context, knowing the location of a gene, or the transcription start of its mRNA, inherently discloses the position of its accompanying promoter. This also applies to the invention, where the "gB gene promoter from a mammalian herpesvirus" refers to the promoter that drives the expression of a herpesvirus gB gene, and is situated immediately upstream of that gB gene. The gB protein in normal herpesvirus replication is involved in cell-entry and cell-spread. Because the gB gene is such a well documented and clearly recognisable gene, and because the genomes of many herpesvirideae have been sequenced (in whole or in part), the skilled person can readily identify and obtain such a promoter by routine techniques.

A review of herpesvirus gB proteins was presented by Perreira (1994, Infect. Agents Dis., vol. 3, p. 9-28). The promoter of the HSV1 gB gene was studied in detail by Pederson et al. (1992, J. of Virol., vol. 66, p. 6226-6232). Neither of these however describe or suggest the use of a herpesvirus gB promoter to drive heterologous gene expression, neither in HVT or in any other expression vector system.

For the invention, the gB gene promoter from a mammalian herpesvirus needs to be able to drive the expression of the HA gene. This is commonly referred to as the promoter being "operatively linked" to the gene, or: the gene being 'under the control of' the promoter. This commonly means that in the final HVT vector construct the gB gene promoter and the HA gene are connected on the same DNA, in effective proximity, and with no signals or sequences between them that would intervene with an effective transcription and translation.

In the vector constructs of the invention, the start codon is provided by the HA gene. Also the vector constructs made were as clean as possible, indicating that except for some restriction enzyme sites, there were no substantive foreign elements in the recombinant vector construct such as an expression cassette with heterologous elements required for cloning or selection of recombinants.

Although not strictly necessary, in a preferred embodiment the HA gene is constructed to contain a downstream polyA signal, for instance from SV40. Such a signal may provide for a more complete termination of transcription, and for polyadenylation of the transcript for translation.

The generation of the HVT+HA vector construct can be done by well-known molecular biological techniques, involving cloning, transfection, recombination, selection, and amplification.

A "mammalian herpesvirus" for the invention relates to a herpesvirus that commonly infects and replicates in a mammalian species. Preferably these are from the taxonomic subfamily of Alphaherpesvirinae. For example: human herpesvirus1 (herpes simplex virus1), bovine herpesvirus1, feline herpes virus1, equine herpesvirus1 (EHV), or pseudorabies virus (PRV, also: suid herpesvirus1).

gB gene promoters from such mammalian herpesviruses are advantageously used for the invention.

Therefore, in a preferred embodiment the gB gene promoter from a mammalian herpesvirus for the invention is from PRV, or EHV.

HVT vectors comprising these gB gene promoters proved to be sufficiently stable both in vitro and in vivo, and when used in a vaccine for poultry were immunologically highly effective in protecting poultry from AI and reducing AIV spread.

Such promoters can conveniently be obtained from the prior art, such as from Genbank, for example for:

PRV, from Genbank acc.nr: BK001744, region 20139-19596 (the PRV gB gene is UI 27 or gII), or EHV, from Genbank acc.nr:: AY665713, region 60709-61570 (the EHV1 gB gene is ORF 33).

In addition, the Genbank accession no. pfam00606 conveniently represents a cluster of herpesvirus gB proteins.

The vector construct HVP311 as described in the examples contained the EHV gB gene promoter (SEQ ID NO: 1), and demonstrated in vitro and in vivo stability. When used as a vaccine, this construct showed a good immune protection and reduction of virus spread, see the Examples.

To improve the efficacy of the gB gene promoter from a mammalian herpesvirus for the invention even further, while maintaining its stability, the promoter was adapted. The adaptation was an elongation of the promoter sequence, such that now it did not end before A+1, but extended downstream of A+1 of the gB gene startcodon, into the coding region of the gB gene that is normally translated into protein.

A result was that the extended promoter now comprised one or more ATG codons, namely the original start codon and possible other Methionine coding triplets. Such ATG codons, in this position downstream of the TATA box in the promoter could be interpreted by the cellular transcription machinery as a start codon, leading to undesired premature initiation of translation. Therefore ATG codons downstream of the TATA-box of the gB gene promoter, that were now comprised in the extended promoter sequence were modified by mutation to make such ATG's non-functional as a potential start codon. This allowed the gB promoter for the invention to incorporate nucleotides that span the native gB start codon and extend into the translated region of the gB gene, however these additional nucleotides are not capable of being translated, but act as an extended leader sequence.

Consequently, promoter sequences were constructed that contained nucleotides from the gB coding region downstream of the original A+1.

Therefore, in a more preferred embodiment the gB gene promoter from a mammalian herpesvirus comprises nucleotide sequences from the translated region of said gB gene, wherein any ATG nucleotide sequence was changed.

The 'change' of the ATG nucleotide sequence in the extended promoter for the invention, is preferably made by mutation. The ATG nucleotide sequence can be changed in principle to any other triplet, as long as this does not reduce the stability in replication, or the expression from the vector construct.

Preferably the change is by a single nucleotide, preferably from ATG to TTG.

The number of nucleotides downstream of ATG that are comprised in an extended gB promoter for the invention is at least 10, preferably at least 20, 30, 50, 75 or 100, in that order of preference. In practice, the number of nucleotides downstream of A+1 that are to be incorporated into the extended promoter for the invention, can conveniently be taken as the sequence from A+1 up to—but not including—the next downstream ATG codon. In that case only one ATG sequence (that of the start codon) needs to be changed by mutation.

The vector construct HVP310 as described in the examples contains a PRV gB gene promoter extended for 129 nt past A+1. The only ATG sequence comprised in the extended sequence was from the original start codon, this was changed into TTG by mutation. This vector showed a similar efficacy and stability in vitro as the unadapted EHV gB gene promoter, however with a much improved efficacy in vivo, see the Examples.

The extended PRV gB gene promoter is as presented in: SEQ ID NO: 2.

Therefore in a further preferred embodiment of the gB gene promoter from a mammalian herpesvirus according to the invention, the promoter has a nucleotide sequence as in SEQ ID NO: 2, or its equivalent.

The HA gene that is comprised in an HVT vector according to the invention, can in principle be any influenza virus HA gene, thus in principle from any IV, and of any serotype H1-H16, or similar HA genes described in the future.

For optimal efficacy of the vaccine for poultry against AI that is based upon the HVT vector of the invention, the inserted HA gene is preferably a highly pathogenic (HP) type HA gene, thus comprising the basic amino acids at the HA1-HA2 cleavage site. The expression of an HP HA gene provides the possibility to vaccinate poultry effectively against an infection with an HP type AIV, and reduce further spread into the environment.

Therefore, in a further preferred embodiment of the HVT vector according to the invention, the nucleotide sequence capable of encoding an IV HA protein was derived from an HP IV.

It is well known in the art, which IV's qualify as being HP, and many sequences are publicly available. Also, HP HA genes for use in the invention can readily be obtained from field isolates of HP IV, from different species of hosts, using routine molecular biological techniques such as RT-PCR.

Preferably, the HP type HA for the invention is obtained from an HP AIV.

NB: Working with live HP AIV isolates will require laboratory facilities of an appropriate containment level.

To further improve the efficacy of a vaccine for poultry comprising the HVT vector according to the invention, the HA gene comprised in this vector was subjected to codon optimisation. The process of codon optimisation is well known in the art, and involves the adaptation of a nucleotide sequence encoding a protein to encode the same amino acids as the original coding sequence, be it with other nucleotides; i.e. the mutations are essentially silent. This improves the level at which the coding sequence is expressed in a context that differs from the origin of the expressed gene. For instance when expressing a certain gene in the new context of a recombinant expression system, the adapted codon usage then accommodates the codon preference of the new system. In practice this will mean that while most amino acids will remain the same, the encoding nucleotide sequence may differ considerably (up to 25% identity) from the original sequence.

For the invention, the coding sequence of the cDNA of the IV HA gene used in the invention was optimised for expression in a eukaryotic viral vector, such as HVT.

Examples of HA gene sequences from HP type AIV's, that have been codon-optimised for the invention are: SEQ ID NO's: 3 and 3, from H5 and H7 HA genes respectively, and the corresponding encoded HA proteins in SEQ ID NO: 4 and 6. As is well known, HA proteins that are within 90% amino acid sequence identity of these genes are commonly considered to be of the same antigenic class.

Therefore in a more preferred embodiment of the nucleotide sequence capable of encoding the IV HA protein for the HVT vector according to the invention, the encoded AIV HA protein has at least 90% amino acid sequence identity to the amino acid sequence as in SEQ ID NO 4, or 6. Even more preferred 95, 96, 97, 98, 99, or 100%, in that order of preference.

In a further preferred embodiment, the nucleotide sequence capable of encoding the IV HA protein for the invention has a nucleotide sequence that has at least 90% nucleotide sequence identity to the nucleotide sequence as in SEQ ID NO: 3 or 5. Even more preferred 95, 96, 97, 98, 99, or 100%, in that order of preference.

The most preferred HVT vector according to the invention comprises a heterologous nucleic acid which comprises an extended gB gene promoter, from PRV (e.g. SEQ ID NO: 2) and a codon-optimised AIV HA gene, of an H5 type (e.g. SEQ ID NO: 3), whereby this heterologous nucleic acid is inserted into the HVT genome in the Us2 locus.

An example of such an HVT+HA vector virus is represented by the HVP310 vector construct (see Examples), which provided the highest efficacy in immunisation and reduction of viral spread measured.

The nucleotide sequence of a heterologous nucleic acid that can be used to assemble such a recombinant HVT+HA vector virus by routine techniques is as presented in SEQ ID NO: 7. The sequence can conveniently be incorporated into a standard carrier plasmid such as commercially available from the pUC series. The resulting plasmid is then commonly referred to as a 'transfervector', and is suitable for use in transfection protocols.

As described, the HVT+HA vector construct according to the invention can be generated by standard techniques well known in the art. Central to these techniques is the integration into the genome of an HVT, of a heterologous nucleic acid comprising a gB gene promoter from a mammalian herpesvirus and an IV HA gene, both according to the invention.

Therefore a further aspect of the invention relates to a method for the preparation of the HVT vector according to the invention, comprising the integration into the genome of an HVT of a heterologous nucleic acid which comprises a nucleotide sequence capable of encoding an IV HA protein, wherein said nucleotide sequence is operatively linked to a gB gene promoter from a mammalian herpesvirus.

The advantageous use of the HVT+HA vector according to the invention is in a vaccine for poultry against AI; protecting the birds and their surroundings from infection and disease caused by AIV.

Therefore, in a further aspect the invention relates to the HVT vector according to the invention, or to the HVT vector as obtainable by the method of the invention, for use in the vaccination of poultry against AI.

Such use in the vaccination according to the invention, is advantageously performed by using a vaccine composition comprising the HVT vector according to the invention.

Therefore, in a further aspect the invention relates to the HVT vector according to the invention, or to the HVT vector as obtainable by the method of the invention, for use in a vaccine against AI in poultry.

Such use of the vector according to the invention is embodied in a vaccine for poultry.

Therefore in a further aspect the invention relates to a vaccine against AI in poultry, comprising the HVT vector according to the invention, or as obtainable by the method of the invention, and a pharmaceutically acceptable carrier.

A vaccine is well known to be a composition comprising an immunologically active compound, in a pharmaceutically acceptable carrier. The 'immunologically active compound', or 'antigen' is a molecule that is recognised by the immune system of the target and induces an immunological response. The response may originate from the innate or the acquired immune system, and may be of the cellular and/or the humoral type. For the present invention, the antigen is a protein.

In general a vaccine induces an immune response that aids in preventing, ameliorating, reducing sensitivity for, or treatment of a disease or disorder resulting from infection with a micro-organism. The protection is achieved as a result of administering at least one antigen derived from that micro-organism. This will cause the target animal to show a reduction in the number, or the intensity of clinical signs caused by the micro-organism. This may be the result of a reduced invasion, colonization, or infection rate by the micro-organism, leading to a reduction in the number or the severity of lesions and effects that are caused by the micro-organism or by the target's response thereto.

The "pharmaceutically acceptable carrier" is intended to aid in the effective administration of a compound, without causing (severe) adverse effects to the health of the animal to which it is administered. Such a carrier can for instance be sterile water or a sterile physiological salt solution. In a more complex form the carrier can e.g. be a buffer, which can comprise further additives, such as stabilisers or conservatives. Details and examples are for instance described in well-known handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

The vaccine according to the invention is prepared from live HVT+HA viral vector particles according to the invention by methods as described herein, which are readily applicable by a person skilled in the art. For example, the HVT+HA vector according to the invention is constructed by transfection and recombination and the desired recombinant HVT vector is selected as described herein. Next the HVT vector viruses are produced industrially in smaller or larger volumes. Although production in host animals is possible, proliferation in in vitro cultures, e.g. in CEF's, is preferred. After harvesting a suspension comprising the virus, either whole cells or a cell-sonicate, this suspension is formulated into a vaccine and the final product is packaged. After extensive testing for quality, quantity and sterility such vaccine products are released for sale.

General techniques and considerations that apply to vaccinology are well known in the art and are described for instance in governmental regulations (Pharmacopoeia) and in handbooks such as: "Veterinary vaccinology" and: "Remington" (both supra).

The HVT+HA vector vaccine according to the present invention in principle can be given to target poultry by different routes of application, and at different points in their lifetime, provided the inoculated HVT+HA vector virus can establish a protective infection.

However, because an infection with AIV can be established already at very young age, it is advantageous to apply the vaccine according to the invention as early as possible. Therefore, the vaccine according to the invention is preferably applied at the day of hatch ("day 1"), or in ovo, e.g. at 18 days ED. In addition, application is preferably by a method of mass vaccination. This provides the earliest possible protection, while minimising labour cost.

Well known methods for such mass application routes applicable at early age, are: by coarse spray at day 1, or by automated injection into the egg. Suitable equipment for industrial scale application is available commercially.

Therefore, in a further preferred embodiment, the vaccine according to the invention can be applied in ovo.

Different in ovo inoculation routes are known, such as into the yolk sac, the embryo, or the allantoic fluid cavity; these can be optimised as required. Preferably inoculation is into the allantoic fluid cavity.

Alternatively, when the vaccine according to the invention is to be combined with a further antigenic component, a parenteral application may be required, e.g. by injection into or through the skin: e.g. intramuscular, intraperitoneal, subcutaneous, etc.

Formulations of the vaccine according to the invention suitable for injection, are e.g. a suspension, solution, dispersion, or emulsion.

When applied by spray vaccination, the droplet size used is important; generally a coarse spray is applied (droplet size of over 50 μm), which effectively is an application by oral, nasal, and/or ocular route.

Depending on the route of application of the vaccine according to the invention, it may be necessary to adapt the vaccine composition. This is well within the capabilities of a skilled person, and generally involves the fine-tuning of the efficacy or the safety of the vaccine. This can be done by adapting the vaccine dose, quantity, frequency, route, by using the vaccine in another form or formulation, or by adapting the other constituents of the vaccine (e.g. a stabiliser or an adjuvant).

For example, to be suitable for application in ovo, the vaccine composition is required to be very mild, in order not to reduce the hatchability of the eggs. Some reduction of hatchability can be acceptable, e.g. by 10%, more preferably 5, 4, 3, 2, 1 or 0% in that order of preference.

In general the safety of the vaccine according to the invention is provided by employing as parental HVT virus for the vector construct according to the invention, an established safe HVT vaccine strain, such as a PB1 or FC126 HVT strain. These are generally available and known to be suitable for in ovo inoculation. The incorporation of a heterologous nucleic acid is not likely to increase its virulence or pathogenicity (on the contrary), and no return to virulence is applicable.

The exact amount of HVT vector viruses according to the invention in a vaccine dose is not as critical as it would be for a inactivated emulsion type vaccine, because the HVT vector virus will replicate itself and thus multiply in the host up to a level of viraemia that is biologically sustainable. The vaccine dose only needs to be sufficient to generate such a productive infection. A higher inoculum dose hardly shortens the time it takes to reach the optimal viraemia in the host; very high doses are not effective in that the viraemia that establishes cannot be higher than the natural optimum, in addition such a very high inoculum dose is not attractive for economic reasons.

A preferred inoculum dose is therefore between 1×10^0 and 1×10^6 plaque forming units (pfu) of HVT vector viruses per animal-dose, more preferably between 1×10^1 and 1×10^5/pfu dose, even more preferably between 1×10^2 and 1×10^4/pfu dose; most preferably between 500 and 5000 pfu/dose.

Determination of the immunologically effective amount of the vaccine according to the invention is well within reach of the skilled person, for instance by monitoring the immunological response following vaccination, or after a challenge infection, e.g. by re-isolation of the pathogen, or by monitoring the targets' clinical signs of disease, or serological parameters, and comparing these to responses seen in unvaccinated animals.

The dosing scheme for applying the vaccine according to the invention to a target organism can be in single or multiple doses, which may be given at the same time or sequentially, in a manner compatible with the formulation of the vaccine, and in such an amount as will be immunologically effective.

The vaccine according to the invention can be used both for prophylactic and for therapeutic treatment, and so interferes either with the establishment and/or with the progression of an infection or its clinical symptoms of disease.

The vaccine according to the invention may effectively serve as a priming vaccination, which can later be followed and amplified by a booster vaccination, for instance with a classical inactivated whole virus, adjuvanted vaccine.

The protocol for the administration of the vaccine according to the invention ideally is integrated into existing vaccination schedules of other vaccines.

Preferably the vaccine according to the invention is applied only once, at the day of hatch, or in ovo.

The volume per animal dose of the HVT+HA vector vaccine according to the invention can be optimised according to the intended route of application: in ovo inoculation is commonly applied with a volume between 0.05 and 0.5 ml/egg, and parenteral injection is commonly done with a volume between 0.1 and 1 ml/bird.

The determination, and the optimisation of the dosage volume is well within the capabilities of the skilled artisan.

It is highly efficient to formulate the vaccine according to the invention as a combination-vaccine, as in this way multiple immunologic agents can be administered at once, providing reduction of time- and labour costs, as well as reduction of discomfort to the vaccinated target animals. A combination vaccine comprises in addition to the vaccine according to the invention, another antigenic compound. In principle this can be any live or killed micro-organisms or subunit product, provided this does not reduce the stability in replication, or the expression from the HVT+HA vector construct. The additional immunoactive component(s) may be an antigen, an immune enhancing substance, a cytokine, and/or a vaccine Alternatively, the vaccine according to the invention, may itself be added to a vaccine.

Therefore, in a further preferred embodiment, the vaccine according to the invention is characterised in that the vaccine comprises one or more additional immunoactive component(s).

In a more preferred embodiment the vaccine according to the invention is a combination vaccine, comprising at least one additional antigen from a micro-organism that is pathogenic to poultry.

Preferably the additional antigen from a micro-organism that is pathogenic to poultry is selected from the groups consisting of:

viruses: infectious bronchitis virus, Newcastle disease virus, Adenovirus, Egg drop syndrome virus, Infectious bursal disease virus (i.e. Gumborovirus), chicken anaemia virus, avian encephalo-myelitis virus, fowl pox virus, turkey rhinotracheitis virus, duck plague virus (duck viral enteritis), pigeon pox virus, MDV, avian leucosis virus, ILTV, avian pneumovirus, and reovirus;

bacteria: *Escherichia coli, Salmonella* spec., *Ornitobacterium rhinotracheale, Haemophilis paragallinarum, Pasteurella multocida, Erysipelothrix rhusiopathiae, Erysipelas* spec., *Mycoplasma* spec., and *Clostridium* spec.;

parasites: *Eimeria* spec.; and fungi: e.g. *Aspergillus* spec.

Most preferred are MDV, ILTV, IBDV, and NDV.

The preferred poultry target animals for the application of the vaccine according to the invention, are chickens. Said chickens may be layers, breeders, combination breeds, or parental lines of any of such chicken breeds.

The age, weight, sex, immunological status, and other parameters of the poultry to be vaccinated are not critical, although it is evidently favourable to vaccinate healthy targets, and to vaccinate as early as possible to prevent any field infection.

The vaccine according to the invention is advantageously used in a DIVA approach, as a 'marker vaccine'. A marker vaccine is known as a vaccine that allows the discrimination between vaccinated and field-infected subjects. This can conveniently be detected by a serological assay such as an ELISA or immuno-fluorescence assay.

Therefore, in a preferred embodiment, the vaccine according to the invention is a marker vaccine.

As described, there are various ways the vaccine according to the invention can be composed and formulated, depending on the desired route of application, antigenic combination, etc.

Therefore, in a further aspect the invention relates to the use of the HVT vector according to the invention, or to the HVT vector as obtainable by the method of the invention, for the manufacture of a vaccine against AI in poultry.

Alternatively, in a further aspect the invention relates to a method for the preparation of the vaccine according to the invention, the method comprising the admixing of the HVT vector according to the invention, or to the HVT vector as obtainable by the method of the invention, and a pharmaceutically acceptable carrier.

Because of the advantageous properties of HVT, the vaccine manufactured according to the use or the method of the invention, can be presented in different forms, in particular in cell-free or in cell-associated form. To obtain the cell associated form, the HVT+HA vector virus is harvested along with its host cells in which it was produced, e.g. CEF's. In the cell-free form, the host production cells are sonicated in a stabiliser solution, and the cell-free HVT are harvested as the supernatant of the sonicate.

The vaccine according to the invention may be manufactured to contain one or more components that aid the viability and quality of the HVT vector according to the invention, thereby promoting the productive replication and establishment of a protective infection in target poultry.

Therefore, in a preferred embodiment, the vaccine manufactured according to the use or the method of the invention comprises a stabiliser.

Stabilisers are compounds that stabilise the quantity and the quality of the HVT vector according to the invention during storage, handling, and inoculation, such as by injection or ingestion. Generally these are large molecules of high molecular weight, such as lipids, carbohydrates, or proteins; for instance milk-powder, gelatine, serum albumin, sorbitol, trehalose, spermidine, dextrane or polyvinyl pyrrolidone.

Also preservatives may be added, such as thimerosal, merthiolate, phenolic compounds, or gentamicin.

In a preferred embodiment, the compounds used for the manufacture of the vaccine composition according to the invention are serum free (i.e. without animal serum); protein free (without animal protein, but may contain other animal derived components); animal compound free (ACF; not containing any component derived from an animal); or even 'chemically defined', in that order of preference.

It goes without saying that admixing other compounds, such as carriers, diluents, emulsions, and the like to vaccines according to the invention are also within the scope of the invention. Such additives are described in well-known handbooks such as: "Remington", and "Veterinary Vaccinology" (both supra).

For reasons of stability or economy a vaccine according to the invention may be manufactured in freeze-dried form. In general this will enable prolonged storage at temperatures above zero ° C., e.g. at 4° C. Procedures for freeze-drying are known to persons skilled in the art, and equipment for freeze-drying at different scales is available commercially.

Therefore, in a further preferred embodiment, the vaccine manufactured according to the use or to the method of the invention is in a freeze-dried form.

To reconstitute a freeze-dried vaccine composition, it is commonly suspended in a physiologically acceptable diluent. Such a diluent can e.g. be as simple as sterile water, or a physiological salt solution, e.g. phosphate buffered saline (PBS); alternatively the diluent may contain an adjuvating compound, such as a tocopherol, as described in EP 382,271. In a more complex form the freeze-dried vaccine may be suspended in an emulsion e.g. as described in EP 1,140,152.

As described, the vaccine according to the invention can advantageously be applied to poultry by a method of vaccination such as by spray, inoculation or in ovo application.

Therefore, in a further aspect the invention relates to a method of vaccination of poultry against avian influenza, comprising the step of inoculating said poultry with a vaccine according to the invention.

The invention will now be further described with reference to the following, non-limiting, examples.

EXAMPLES

1. Assembly of Vector Constructs 1.1. HVP142

HVT vector viruses of HVP142 carry as a heterologous insert, an H5 IV gene, driven by the RSV LTR promoter. The transfection cassette was inserted into the US10 locus of HVT strain PB1, using the homologous recombination technique. The H5 gene was obtained from an H5N2 AIV isolate from 1998.

Methods for transfection, recombination, selection and amplification were essentially as described in Sondermeijer et al., 2003 (supra), and EP 431,668.

Antiserum used for selection of HA expressing plaques was a polyclonal chicken antiserum against an H5N6 type AIV strain.

1.2. HVP310

HVP310 vector viruses comprised a codon optimised H5 gene (SEQ ID NO: 3), which was driven by a PRV gB gene promoter that had been extended downstream of the gB gene ATG startcodon (SEQ ID NO: 2). The heterologous construct was inserted into the Us2 locus of the HVT genome of strain FC126, by using a cosmid clone regeneration technique. The total expression construct was as represented in SEQ ID NO: 7.

The H5 gene originated from an HP H5N1 isolate taken from an Asian cat from 2005. This had been amended by codon usage optimisation for expression in a viral expression vector system.

Methods for transfection, recombination, selection and amplification were essentially as described in U.S. Pat. No. 5,961,982. Transfected CEF cells after recombination were seeded in 10 cm tissue culture plates; after about 1 week plaques became clearly visible. Plaques were counterstained with Evans blue, and plaques could be picked directly from the plates. DNA from recombinant HVT vector viruses was routinely checked for correctness of recombination and insertion of HA gene and promoter by restriction enzyme analysis.

Expression of the integrated HA gene was done by immunofluorescence assay in microtitration plates, using H5N6 chicken polyclonal antiserum.

1.3. HVP311

HVP311 vector viruses comprised a codon optimised H5 gene, which was driven by an EHV gB gene promoter (SEQ ID NO: 1). Construction, recombination, and selection was similar to that for HVP310 virus. Also, the same codon optimised H5 HA gene insert was used.

1.4. Stability Testing In Vitro

To determine in vitro stability, recombinant HVT vector viruses HVP142, 310 and 311 were passaged for at least 15 times on CEF monolayers. After one plaque was picked, this was amplified 15 rounds.

Finally, 10 cm plates were inoculated and after incubation, stained with chicken H5N6 antiserum for an immunofluorescence test (IFT). The number of plaques showing positive immunofluorescence per total number of plaques were counted. All recombinants tested were found to be completely stable in in vitro cultures as 100% of the plaques displayed positive fluorescence. This meant that firstly the HA insert had been correctly replicated through the more than 15 cell-culture passages, and secondly, that the HA gene was still intact and being expressed correctly.

2. Animal Trial in SPF Chickens 2.1. Setup of Animal Trial

The animal-experiment was set up to determine the efficacy of HVT+HA recombinants following vaccination of one-day-old specific pathogen free (SPF) broiler chicks. Protective-efficacy was assessed by challenge-infection with an HPAI H5N1 virus at two or at three weeks post vaccination (p.v.). Chicks were observed daily for the occurrence of clinical signs of avian influenza infection or mortality. In addition, tracheal and cloacal swabs were collected to assess challenge virus excretion by PCR.

Groups of 10 SPF broiler chicks were placed in negative pressure isolators in the high-containment facilities of the central veterinary institute (Lelystad, NL). Bloodsamples were taken weekly through the course of the trail.

Vaccines tested were the recombinant HVT vector viruses HVP142, 310, and 311, next to a conventional inactivated emulsion vaccine of H5 type, and a mock vaccinated group receiving only PBS. The recombinant HVT vaccines had been prepared as cell-associated preparations at about 5×10^5 pfu/ml, which were stored in liquid nitrogen until use.

Chickens were placed, marked individually, and vaccinated; HVT was administered intramuscular, with 0.2 ml/dose at 2000 pfu/chick.

After two or three weeks chicks were challenged with 10^6.0 EID50 per chick of HP AIV H5N1 challenge virus (H5N1 Turkey/Turkey/01/05 Clade 2.2), with 0.1 ml via the nasal route and 0.1 ml via the intra-tracheal route.

After challenge chickens were observed daily for signs of AI. Clinical scores were awarded ranging from 0-3 (none-severe) for typical AI symptoms such as depression, oro-nasal discharge, respiratory distress, neurological signs, diarrhoea, etc. Severely ill chicks were euthanized. Dead chicks were tested by histopathology for cause of death.

Serum samples from before challenge and from 14 days post challenge were determined by heamagglutination inhibition (HI) test using mostly the HPAI H5 type challenge virus.

For the assessment of challenge virus spread, the trachea and the cloaca of each chicken was swabbed at 2, 3, 4, 7 and 14 days post challenge. Swabs were examined individually by Q-PCR on the AIV Matrix protein gene, to compare if, and how much (Ct value) of the challenge virus was shed by the vaccinated and control chickens.

2.2. Results

The results of the trials in SPF chickens are presented in Tables 1-3.

With regard to the 'protection from clinical signs', as presented in Table 2, only those animals that did not show any clinical signs of AI were scored as protected.

In Table 3 the 'positive in viral re-isolation' indicates from which animals it was possible to re-isolate virus; only if an animal was positive for two consecutive days was it listed as positive in virus-reisolation. As none of the cloaca swap samples was ever positive, only trachea-swap results are presented.

TABLE 1

HI titers before challenge, in SPF vaccinated i.m. at day old

| | | HI (log2, HP H5N1 ag.) | |
|---|---|---|---|
| Vaccine | no. animals | chall. at 2 wks p.v. | chall. at 3 wks p.v. |
| HVP142 | 20 | <4 | <4 |
| HVP310 | 20 | 5.9 | 8.6 |
| HVP311 | 20 | 4.2 | 8.1 |
| H5 inac | 20 | <4 *) | <4 *) |
| diluent | 10 | <4 | <4 |

*) When tested in an HI test with an other H5 type antigen, there was clear proof of seroconversion, with HI titers of 6.7 and 8.6, at 2 and 3 weeks p.v. respectively.

TABLE 2

Protection against AI clinical signs, in SPF, vaccinated i.m. at day old, after lethal challenge (<48 h) with HP AIV H5N1.

| | | Protection against clinical signs | |
|---|---|---|---|
| Vaccine | no. animals | chall. at 2 wks p.v. | chall. at 3 wks p.v. |
| HVP142 | 20 | 0/10 | 1/10 |
| HVP310 | 19 | 10/10 | 9/9 |
| HVP311 | 20 | 10/10 | 10/10 |
| H5 inac | 20 | 3/10 | 8/10 |
| diluent | 10 | 0/5 | 0/5 |

TABLE 3

Protection against virus re-isolation, in SPF, vaccinated i.m. at day old, after lethal challenge (<48 h) with HP AIV H5N1.

| | | Positive in virus re-isolation (trachea) | |
|---|---|---|---|
| Vaccine | no. animals | chall. at 2 wks p.v. | chall. at 3 wks p.v. |
| HVP142 | 20 | 10/10 | 10/10 |
| HVP310 | 20 | 6/10 | 1/10 |
| HVP311 | 20 | 6/10 | 2/10 |
| H5 inac | 20 | 10/10 | 10/10 |
| diluent *) | 0 | — | — |

*) Animals in the diluent group could not be swabbed as all died within 48 hours. post challenge 3. Animal Trial in MDA+ Chickens 3.1. Setup of Animal Trial The layout of the animal trial in MDA+ broiler chicks was largely the same as that for the SPF chicken trial except that: HVP142 vector vaccine was not included. The MDA+ broiler chicks were derived from parents that had been vaccinated twice with a conventional inactivated H5N2 emulsion vaccine; chicks had starting H5 HI titers between 5 and 6.

3.2. Results

The results of the trials in MDA+ chickens are presented in Tables 4-6.

For Tables 5 and 6 the same remarks apply as for Tables 2 and 3 above.

TABLE 4

HI titers at day of challenge, in MDA+ vaccinated i.m. at day old

| | | HI (log2, HP H5N1 ag.) | |
|---|---|---|---|
| Vaccine | no. animals | chall. at 2 wks p.v. | chall. at 3 wks p.v. |
| HVP310 | 20 | <4 | 5.4 |
| HVP311 | 20 | <4 | 4.4 |
| H5 inac | 20 | <4 | <4 |
| diluent | 10 | <4 | <4 |

TABLE 5

Protection against AI clinical signs, in MDA+, vaccinated i.m. at day old, after lethal challenge (<120 h) with HP AIV H5N1.

| | | Protection against clinical signs | |
|---|---|---|---|
| Vaccine | no. animals | chall. at 2 wks p.v. | chall. at 3 wks p.v. |
| HVP310 | 20 | 1/10 | 9/10 |
| HVP311 | 19 | 0/10 | 4/9 |
| H5 inac | 18 | 0/9 | 0/9 |
| diluent | 20 | 0/10 | 0/10 |

TABLE 6

Protection against virus re-isolation, in MDA+, vaccinated i.m. at day old, after lethal challenge (<120 h) with HP AIV H5N1.

| | | Positive in virus re-isolation (trachea) | |
|---|---|---|---|
| Vaccine | no. animals | chall. at 2 wks p.v. | chall. at 3 wks p.v. |
| HVP310 | 20 | 10/10 | 7/10 |
| HVP311 | 19 | 10/10 | 9/9 |
| H5 inac | 18 | 9/9 | 9/9 |
| diluent | 20 | 10/10 | 10/10 |

3.3. Quantification by Q-PCR

In the animal trial where MDA+ chickens were challenged, virus re-isolation samples were obtained by swabbing the trachea at day 2 and 3 after challenge. Next nucleic acids were extracted, and real-time RT-PCR assays were performed as described by Maas et al. (2007, Emerging Infectious Diseases, vol. 13, p. 1219-1221). Threshold values (Ct) were expressed in relative copy numbers and compared to value measured in birds that were not vaccinated (control) or were vaccinated with an emulsion vaccine. The copy number corresponding with the lowest Ct value in this group was arbitrarily set at 1000.

FIG. 1 displays the results: a reduction in replication of challenge virus of about 250-fold with strain HVP310.

4. Conclusions of Animal Trial Results 4.1. General:

HVP142 lacked efficacy in SPF trial and was not included in the MDA+ trial.

The HVP310 and 311 vector viruses replicated well, both in SPF and in MDA+ chicks, indicating their stable, viable constitution. The expression of the inserted HA gene was equally stable and effective, as demonstrated by the highly effective immune response that was generated.

The challenge infection applied turned out to be extremely heavy, considering that all controls and many of the vaccinates with conventional emulsion vaccine died. However, this enabled the HVT+HA vector vaccines to demonstrate their protective capacities under the most stringent conditions.

4.2. SPF Trial:

The clinical protection induced in SPF chicks was very impressive: SPF chicks vaccinated with HVP310 and 311 were fully protected against any and all clinical signs of AI, already at 2 weeks post vaccination, whereas the emulsion vaccine provided only partial protection, and non-vaccinated chicks died within 48 hours.

SPF chicks were also almost completely protected from spread of the challenge virus, as demonstrated by virus reisolation results; reduction in virus isolation of 80 and 90% were reached for HVP 311 and 310 respectively, while no reduction in virus spread could be reached by the emulsion vaccine.

The efficacy of HVP310 and 311 vectors in SPF chicks thus differed only minimally.

4.3. MDA+ Trial:

The protection of MDA+ chicks from clinical signs of AI after challenge was much better at 3 weeks p.v. than at 2 weeks p.v. HVP 310 could protect 90% of the MDA+ chicks from showing any clinical signs; HVP311 only reached 45% protection, while the emulsion vaccine did not protect. All non-vaccinated MDA+ chicks died within 120 hours.

Under the harsh conditions of the trial, the HVP310 vector vaccine could still manage to reduce viral spread in MDA+ chicks by 30% at 3 weeks post vaccination, while no reduction in virus spread could be reached by the HVP311 or emulsion vaccines.

The reduction in viral shedding induced by vaccine vector HVP310, relative to emulsion vaccinated, and control vaccinated birds, to be a factor 250 at day 2 post challenge.

5. Stability Test of Re-Isolated Vaccine Virus:

HVP310 and HVP311 vector vaccine will be reisolated from chickens at 2 and 3 weeks after vaccination. Virus will be seeded on 10 cm dishes of CEF, and left to infect. At 5-7 days, plaques will be stained by IFT with chicken H5N6 antiserum, as described. The number of plaques-versus-the number of fluorescent positive plaques will indicate whether all viruses still contain and express the inserted HA gene.

6. Safety of Use for In Ovo Vaccination:

To test the safety for in ovo use of the HVT vector vaccine HVP310 and 311, these will be used in ovo.

Three days before the start of the experiment (t=−3 days) three groups of 40 18-day-old embryonated chicken eggs will be inoculated with the vector vaccines HVP310 and 311, as follows:

Before vaccination the eggs will be candled. The blunt end of 18-day old embryonated eggs will be disinfected with 70% ethanol. A hole will be drilled into the eggshell using an egg driller. The eggs will be vaccinated by inserting a needle (Becton & Dickinson Plastipak® 1 ml syringes and Microlance® 23G, 0.6×25 needles) vertically into the egg and injecting 0.05 ml of the vaccines. Subsequently the holes will be sealed with glue and the eggs will be placed in incubators, under appropriate conditions.

Next the eggs will hatch in three incubators in animal facilities. After hatching, 25 chickens per group will be tagged and placed in group 1 to 3 (t=1 day), and housed in three isolators respectively, and observed for another week.

The outcome numbers and the health of the chickens hatched will be monitored to determine if any effect on hatchability or health occurs by the in ovo inoculation of HVT vector vaccine HVP310 and 311.

7. Difference in Properties of gB Gene Promoters Derived from Avian- or from Mammalian Herpesvirus, when Used in an HVT Vector:

When different promoters were tested for their suitability to drive the expression of a heterologous gene in the context of an HVT viral vector, the gB gene promoter from MDV1 proved to be ineffective in HVT. On the other hand, the gB gene promoter from Equine herpes virus (EHV) was operative in HVT.

The constructs used for this purpose were assembled essentially as described in Example 1, and comprised a gene from an *Eimeria tenella* parasite, the Etsc2 gene. This gene encodes an antigen of about 37 kDa, that is the homolog of the Easc2 antigen from *Eimeria acervulina* that is described e.g. in EP 775.746. Transfervector constructs were made that contained the Etsc2 gene under control of the gB gene promoter from either EHV1 (in transfervector construct pVEC102), or from MDV1 (construct pVEC103).

Recombinant HVTs were generated by transfection and homologous recombination, and seeded onto CEF monolayers as described. Recombinant HVT plaques were picked, and these were tested for expression of the Etsc2 antigen, by immuno-fluorescence assay on 96 well plates with CEF cell monolayers. From both constructs two plaques were tested, and each plaque was tested in duplo. A rabbit anti-Etsc2 antiserum was used as primary antibody, followed by a FITC conjugated secondary antibody. This initial screening revealed weakly positive fluorescence for pVEC102 recombinants, but no fluorescence from pVEC103 recombinants.

Next all 4 plaques were amplified, and the IFA was repeated. This time all plaques from pVEC102 (using the EHV gB gene promoter) were clearly positive for Etsc2 antigen expression; however, pVEC103 recombinant plaques remained negative for Etsc2 antigen expression, even though HVT plaques were clearly visible.

It was concluded that the MDV1 gB gene promoter is not effective in the context of a recombinant HVT vector virus, whereas the EHV gB gene promoter is.

Legend to the Figures

FIG. 1:

MDA-plus chickens were vaccinated at day-old, and subsequently challenged. The reduction in viral shedding in as induced by vaccine vector HVP310, relative to emulsion vaccinated, and control vaccinated birds, was found to be a factor 250 at day 2 post challenge.

The invention claimed is:

1. A recombinant herpes virus of turkeys (HVT) vector comprising a heterologous nucleic acid, wherein said heterologous nucleic acid comprises an extended mammalian herpesvirus glycoprotein B (gB) gene promoter operably linked to a nucleotide sequence which encodes an influenza virus (IV) hemagglutinin (HA) protein, wherein the extended mammalian herpesvirus gB gene promoter comprises the nucleotide sequence as in SEQ ID NO: 2.

2. The recombinant HVT vector according to claim 1, wherein the nucleotide sequence encoding an IV HA protein is derived from an avian IV (AIV).

3. The recombinant HVT vector according to claim 2, wherein the nucleotide sequence encoding the AIV HA protein, encodes an AIV HA protein that has at least 90% amino acid sequence identity to the amino acid sequence as in SEQ ID NO: 4 or 6.

4. The recombinant HVT vector according to claim 2, wherein the nucleotide sequence encoding the AIV HA protein has a nucleotide sequence that has at least 90% nucleotide sequence identity to the nucleotide sequence as in SEQ ID NO: 3 or 5.

5. A method for the preparation of the recombinant HVT vector according to claim 1, comprising the integration of a heterologous nucleic acid into the genome of an HVT, wherein said heterologous nucleic acid comprises an extended mammalian herpesvirus glycoprotein B (gB) gene promoter operably linked to a nucleotide sequence which encodes an influenza virus (IV) hemagglutinin (HA) protein, wherein the extended mammalian herpesvirus gB gene promoter comprises the nucleotide sequence of SEQ ID NO: 2.

6. An immunogenic composition, comprising the recombinant HVT vector according to claim 1, and a pharmaceutically acceptable carrier.

7. The immunogenic composition according to claim 6, wherein the immunogenic composition can be applied in ovo.

8. A method for the preparation of the immunogenic composition according to claim 6, said method comprising admixing the recombinant HVT vector according to claim 1 with a pharmaceutically acceptable carrier.

9. A method of inducing an immune response in poultry against avian influenza, comprising the step of inoculating said poultry with the immunogenic composition according to claim 6.

* * * * *

SEQUENCE LISTING

```
<160> NUMBER OF SEQ ID NOS: 7

<210> SEQ ID NO 1
<211> LENGTH: 723
<212> TYPE: DNA
<213> ORGANISM: Equine herpesvirus 1

<400> SEQUENCE: 1
```

```
ggcgactgcg gatgcttcgc agcgcaggcg catgtacgcg gagcgtctgt caaagcgttc      60

catcgccagt ttggggcgct gcgtgcgcga acagcgaaga gaactagaaa aaaccctgag     120

agttaacgtg tatggcgaag tgctgctaca tacgtacgta tcgtcctaca acgggttttg     180

cgccaggcgc gggttttgcg cggcggtgag tcgagcgggt accatcatag ataaccgctc     240

tagcacgtcc gcgttcgact cgcatcagtt catgaaggcg gcgctgcttc gccaccccat     300

tgaccagtcg ctcatgccgt ccataacaca caagtttttc gagctgatca acgggcccgt     360

gtttgacaac gctggccaca actttgcgca gccgccaaac acggcattat attacagcgt     420

tgaaaacgtt gggttgttac cgcatctcaa ggaggaacta gctcggttta tgattactgc     480

ggctaaaggt gattggtcaa ttagcgagtt tcaaaggttt tattgctttg agggagtgac     540

aggtgtgacg gccacgcagc ggctggcgtg gaaatatatc ggggagctca tcctagccgc     600

cgcagtattc tcctcggttt tccactgtgg agaggtgcgc ctcctgcgcg cagatcgtac     660

ctacccggac tccagcggcg cacagcgctg cgtgagcggc atttacataa cctacgaggc     720

gtc                                                                   723
```

```
<210> SEQ ID NO 2
<211> LENGTH: 674
<212> TYPE: DNA
<213> ORGANISM: Pseudorabies virus

<400> SEQUENCE: 2

cgctgctgca cacgtacgtg gcggtggccg ccgggttccg cgcacggcgc gcgttctgcg      60

aggccgccgc gcgcgcgggc accgtcgtgg acgagcgcga gacgggctgc ttcgacgcgc     120

acagcttcat gaaggccacg gtgcagcgcc accccgtgga cgccgcgctc ctcccggcgc     180

tcacgcacaa gttcttcgag ctcgtcaacg ggccgctctt cgcgcacgac acgcacgcct     240

tcgcccagtc ccccaacacg gcgctctact ttgcggtgga gaacgtgggc ctcctgccgc     300

acctgaagga ggagctggcg cgcttcatgg tggcccgcga ttggtgcgtc agtgagttcc     360

gcggcttcta ccgcttccag acggccggcg taaccgccac ccagcggcag gcctggcgat     420

atatccgcga gctggtgctg gcggttgcag tcttcaggtc cgtcttccac tgcggggacg     480

tcgaggtcct ccgcgcggat cgcttcgccg gacgcgacgg gctgtacctg acctacgagg     540

cgtcttgccc gctggtggcg gtctttggcg cgggccccgc gggcatcggc ccgggcacca     600

cggcggtgct ggcctcggac gtctttggcc tgctccacac cacgctgctg ctgcgcgggg     660

cgccgtcgcg ctag                                                       674
```

```
<210> SEQ ID NO 3
<211> LENGTH: 1707
<212> TYPE: DNA
<213> ORGANISM: Artificial Sequence
<220> FEATURE:
<223> OTHER INFORMATION: Codon optimised HP AIV H5 HA gene
<220> FEATURE:
<221> NAME/KEY: CDS
<222> LOCATION: (1)..(1704)

<400> SEQUENCE: 3

atg gag aag atc gtc ctc ctg ctg gct atc gtc tcc ctg gtc aag agc       48
Met Glu Lys Ile Val Leu Leu Leu Ala Ile Val Ser Leu Val Lys Ser
1               5                   10                  15

gac cag atc tgc atc ggc tac cac gcc aac aac tct acc gag cag gtg       96
Asp Gln Ile Cys Ile Gly Tyr His Ala Asn Asn Ser Thr Glu Gln Val
            20                  25                  30
```

```
gac acc atc atg gag aag aac gtg acc gtc act cac gcc cag gac atc      144
Asp Thr Ile Met Glu Lys Asn Val Thr Val Thr His Ala Gln Asp Ile
        35                  40                  45

ctc gag aag act cac aac gga aag ctc tgc gac ctc gac ggc gtc aag      192
Leu Glu Lys Thr His Asn Gly Lys Leu Cys Asp Leu Asp Gly Val Lys
    50                  55                  60

cct ctg atc ctg cgt gac tgc tcc gtg gct ggt tgg ctc ctg ggc aac      240
Pro Leu Ile Leu Arg Asp Cys Ser Val Ala Gly Trp Leu Leu Gly Asn
65                  70                  75                  80

ccc atg tgc gac gag ttc ctc aac gtg ccc gag tgg tcc tac atc gtc      288
Pro Met Cys Asp Glu Phe Leu Asn Val Pro Glu Trp Ser Tyr Ile Val
                85                  90                  95

gag aag atc aac ccc gcc aac gac ctg tgc tac cct ggc aac ttc aac      336
Glu Lys Ile Asn Pro Ala Asn Asp Leu Cys Tyr Pro Gly Asn Phe Asn
            100                 105                 110

gac tac gag gag ctc aag cac ctg ctc tcc cgt atc aac cac ttc gag      384
Asp Tyr Glu Glu Leu Lys His Leu Leu Ser Arg Ile Asn His Phe Glu
        115                 120                 125

aag atc cag atc atc ccc aag tcc tcc tgg tcc gac cac gag gct tct      432
Lys Ile Gln Ile Ile Pro Lys Ser Ser Trp Ser Asp His Glu Ala Ser
    130                 135                 140

agc ggt gtg tcc agc gct tgc ccc tac cag ggc cgc tcc agc ttc ttc      480
Ser Gly Val Ser Ser Ala Cys Pro Tyr Gln Gly Arg Ser Ser Phe Phe
145                 150                 155                 160

cgc aac gtc gtg tgg ctg atc aag aag gac aac gct tac cca act atc      528
Arg Asn Val Val Trp Leu Ile Lys Lys Asp Asn Ala Tyr Pro Thr Ile
                165                 170                 175

aag cgc agc tac aac aac act aac cag gag gac ctg ctg gtg ctg tgg      576
Lys Arg Ser Tyr Asn Asn Thr Asn Gln Glu Asp Leu Leu Val Leu Trp
            180                 185                 190

ggc atc cac cac cct aac gac gcc gct gag cag act cgt ctc tac cag      624
Gly Ile His His Pro Asn Asp Ala Ala Glu Gln Thr Arg Leu Tyr Gln
        195                 200                 205

aac cct act agc tac atc tcc gtg gga acc tct acc ctg aac cag agg      672
Asn Pro Thr Ser Tyr Ile Ser Val Gly Thr Ser Thr Leu Asn Gln Arg
    210                 215                 220

ctg gtg ccc aag atc gct acc agg tcc aag gtc aac ggt cag tct ggt      720
Leu Val Pro Lys Ile Ala Thr Arg Ser Lys Val Asn Gly Gln Ser Gly
225                 230                 235                 240

agg atg gag ttc ttc tgg act atc ctg aag ccc aac gac gct atc aac      768
Arg Met Glu Phe Phe Trp Thr Ile Leu Lys Pro Asn Asp Ala Ile Asn
                245                 250                 255

ttc gag tct aac ggt aac ttc atc gct cct gag aac gcc tac aag atc      816
Phe Glu Ser Asn Gly Asn Phe Ile Ala Pro Glu Asn Ala Tyr Lys Ile
            260                 265                 270

gtc aag aag ggt gac tct act atc atg aag tct gag ctg gag tac ggt      864
Val Lys Lys Gly Asp Ser Thr Ile Met Lys Ser Glu Leu Glu Tyr Gly
        275                 280                 285

aac tgc aac acc aag tgc cag acc cct atc ggt gcc atc aac tcc tct      912
Asn Cys Asn Thr Lys Cys Gln Thr Pro Ile Gly Ala Ile Asn Ser Ser
    290                 295                 300

atg cct ttc cac aac atc cac ccc ctg acc atc ggt gag tgc cct aag      960
Met Pro Phe His Asn Ile His Pro Leu Thr Ile Gly Glu Cys Pro Lys
305                 310                 315                 320

tac gtc aag tct aac cgt ctg gtc ctg gct act gga ctg cgt aac tct     1008
Tyr Val Lys Ser Asn Arg Leu Val Leu Ala Thr Gly Leu Arg Asn Ser
                325                 330                 335

ccc cag ggt gag cgc cgt cgt aag aag agg ggc ctc ttc ggt gcc atc     1056
Pro Gln Gly Glu Arg Arg Arg Lys Lys Arg Gly Leu Phe Gly Ala Ile
```

-continued

```
            340                 345                 350

gct ggc ttc atc gag ggt gga tgg cag ggc atg gtg gac ggc tgg tac      1104
Ala Gly Phe Ile Glu Gly Gly Trp Gln Gly Met Val Asp Gly Trp Tyr
        355                 360                 365

ggt tac cac cac agc aac gag cag ggc tcc ggt tac gct gcc gac aag      1152
Gly Tyr His His Ser Asn Glu Gln Gly Ser Gly Tyr Ala Ala Asp Lys
    370                 375                 380

gag tct acc cag aag gct atc gac ggc gtc acc aac aag gtg aac tcc      1200
Glu Ser Thr Gln Lys Ala Ile Asp Gly Val Thr Asn Lys Val Asn Ser
385                 390                 395                 400

atc atc gac aag atg aac acc cag ttc gag gct gtg ggc agg gag ttc      1248
Ile Ile Asp Lys Met Asn Thr Gln Phe Glu Ala Val Gly Arg Glu Phe
                405                 410                 415

aac aac ctg gag cgt cgt atc gag aac ctg aac aag aag atg gag gac      1296
Asn Asn Leu Glu Arg Arg Ile Glu Asn Leu Asn Lys Lys Met Glu Asp
            420                 425                 430

ggt ttc ctg gac gtc tgg act tac aac gcc gag ctc ctg gtg ctg atg      1344
Gly Phe Leu Asp Val Trp Thr Tyr Asn Ala Glu Leu Leu Val Leu Met
        435                 440                 445

gag aac gag cgc acc ctg gac ttc cac gac tcc aac gtg aag aac ctc      1392
Glu Asn Glu Arg Thr Leu Asp Phe His Asp Ser Asn Val Lys Asn Leu
    450                 455                 460

tac gac aag gtc cgc ctc cag ctc cgc gac aac gct aag gag ctg ggt      1440
Tyr Asp Lys Val Arg Leu Gln Leu Arg Asp Asn Ala Lys Glu Leu Gly
465                 470                 475                 480

aac ggt tgc ttc gag ttc tac cac agg tgc gac aac gag tgc atg gag      1488
Asn Gly Cys Phe Glu Phe Tyr His Arg Cys Asp Asn Glu Cys Met Glu
                485                 490                 495

tcc gtg cgt aac ggc acc tac gac tac ccc cag tac tcc gag gag gcc      1536
Ser Val Arg Asn Gly Thr Tyr Asp Tyr Pro Gln Tyr Ser Glu Glu Ala
            500                 505                 510

cgt ctc aag agg gag gag atc tcc ggt gtg cgc ctg gag agc atc ggt      1584
Arg Leu Lys Arg Glu Glu Ile Ser Gly Val Arg Leu Glu Ser Ile Gly
        515                 520                 525

act tac cag atc ctc tcc atc tac tcc acc gtc gcc agc tcc ctc gcc      1632
Thr Tyr Gln Ile Leu Ser Ile Tyr Ser Thr Val Ala Ser Ser Leu Ala
    530                 535                 540

ctg gct atc atg gtg gct ggc ctc tcc ctg tgg atg tgc tcc aac ggc      1680
Leu Ala Ile Met Val Ala Gly Leu Ser Leu Trp Met Cys Ser Asn Gly
545                 550                 555                 560

agc ctg cag tgc aag atc tgc atc taa                                  1707
Ser Leu Gln Cys Lys Ile Cys Ile
                565


<210> SEQ ID NO 4
<211> LENGTH: 568
<212> TYPE: PRT
<213> ORGANISM: Artificial Sequence
<220> FEATURE:
<223> OTHER INFORMATION: Synthetic Construct

<400> SEQUENCE: 4

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60
```

```
Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Ser Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480
```

```
Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Arg Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Lys Ile Cys Ile
                565


<210> SEQ ID NO 5
<211> LENGTH: 1683
<212> TYPE: DNA
<213> ORGANISM: Artificial Sequence
<220> FEATURE:
<223> OTHER INFORMATION: Codon optimised HP AIV H7 HA gene
<220> FEATURE:
<221> NAME/KEY: CDS
<222> LOCATION: (1)..(1680)

<400> SEQUENCE: 5

atg aac act cag atc ctg gta ttc gct ctg gtg gcg atc atc cca acc       48
Met Asn Thr Gln Ile Leu Val Phe Ala Leu Val Ala Ile Ile Pro Thr
1               5                   10                  15

aac gcc gac aag atc tgc ctg gga cac cac gcc gtc tcc aac gga act       96
Asn Ala Asp Lys Ile Cys Leu Gly His His Ala Val Ser Asn Gly Thr
            20                  25                  30

aag gtc aac acc ttg act gag cgt ggc gtg gag gtg gtc aac gct act      144
Lys Val Asn Thr Leu Thr Glu Arg Gly Val Glu Val Val Asn Ala Thr
        35                  40                  45

gag acc gtg gag cgc act aac gtc ccc cgt atc tgc tcc aaa ggt aag      192
Glu Thr Val Glu Arg Thr Asn Val Pro Arg Ile Cys Ser Lys Gly Lys
    50                  55                  60

cgt acc gtg gac ctc ggt cag tgc ggc ctg ctg ggt act atc act ggc      240
Arg Thr Val Asp Leu Gly Gln Cys Gly Leu Leu Gly Thr Ile Thr Gly
65                  70                  75                  80

ccc ccc cag tgc gac cag ttc ctg gag ttc tct gcc gac ctg atc atc      288
Pro Pro Gln Cys Asp Gln Phe Leu Glu Phe Ser Ala Asp Leu Ile Ile
                85                  90                  95

gag cgt cgc gag ggt tcc gac gtc tgc tac cct ggc aag ttc gtg aac      336
Glu Arg Arg Glu Gly Ser Asp Val Cys Tyr Pro Gly Lys Phe Val Asn
            100                 105                 110

gag gag gct ctg cgt cag atc ctc cgc gag tcc ggc ggt atc gac aag      384
Glu Glu Ala Leu Arg Gln Ile Leu Arg Glu Ser Gly Gly Ile Asp Lys
        115                 120                 125

gag acc atg ggc ttc acc tac agc ggt atc cgc act aac ggc gcc acc      432
Glu Thr Met Gly Phe Thr Tyr Ser Gly Ile Arg Thr Asn Gly Ala Thr
    130                 135                 140

tcc gct tgc cgc cgt tcc ggt tct tcc ttc tac gcc gag atg aag tgg      480
Ser Ala Cys Arg Arg Ser Gly Ser Ser Phe Tyr Ala Glu Met Lys Trp
145                 150                 155                 160

ctc ctg tcc agc act gac aac gct gct ttc ccc cag atg act aag tcc      528
Leu Leu Ser Ser Thr Asp Asn Ala Ala Phe Pro Gln Met Thr Lys Ser
                165                 170                 175

tac aag aac acc cgc aag gac cct gct ctg atc atc tgg ggc atc cac      576
Tyr Lys Asn Thr Arg Lys Asp Pro Ala Leu Ile Ile Trp Gly Ile His
            180                 185                 190
```

-continued

```
cac tcc ggt tcc acc act gag cag acc aag ctg tac ggc tcc ggt aac      624
His Ser Gly Ser Thr Thr Glu Gln Thr Lys Leu Tyr Gly Ser Gly Asn
        195                 200                 205

aag ctc atc acc gtc ggc tct tct aac tac cag cag tcc ttc atc ccc      672
Lys Leu Ile Thr Val Gly Ser Ser Asn Tyr Gln Gln Ser Phe Ile Pro
    210                 215                 220

tct ccc ggt gcc cgc cct cag gtg aac ggc cag tct ggc cgc atc gac      720
Ser Pro Gly Ala Arg Pro Gln Val Asn Gly Gln Ser Gly Arg Ile Asp
225                 230                 235                 240

ttc cac tgg ctg atc ctg aac ccc aac gac act atc act ttc tcc ttc      768
Phe His Trp Leu Ile Leu Asn Pro Asn Asp Thr Ile Thr Phe Ser Phe
                245                 250                 255

aac ggt gcc ttc atc gct cct gac cgt gct agc ttc ctg cgt ggc aag      816
Asn Gly Ala Phe Ile Ala Pro Asp Arg Ala Ser Phe Leu Arg Gly Lys
            260                 265                 270

tct atg ggt atc cag tcc ggt gtc cag gtg gac gcc aac tgc gag ggt      864
Ser Met Gly Ile Gln Ser Gly Val Gln Val Asp Ala Asn Cys Glu Gly
        275                 280                 285

gac tgc tac cac tct ggc ggt acc atc atc agc aac ctg ccc ttc cag      912
Asp Cys Tyr His Ser Gly Gly Thr Ile Ile Ser Asn Leu Pro Phe Gln
    290                 295                 300

aac atc aac agc cgc gcc gtc ggc aag tgc cct cgc tac gtc aag cag      960
Asn Ile Asn Ser Arg Ala Val Gly Lys Cys Pro Arg Tyr Val Lys Gln
305                 310                 315                 320

gag tcc ctg atg ctg gct act ggt atg aag aac gtg ccc gag atc cct     1008
Glu Ser Leu Met Leu Ala Thr Gly Met Lys Asn Val Pro Glu Ile Pro
                325                 330                 335

aag ggc cgt ggc ctg ttc ggc gct atc gcc ggt ttc atc gag aac ggt     1056
Lys Gly Arg Gly Leu Phe Gly Ala Ile Ala Gly Phe Ile Glu Asn Gly
            340                 345                 350

tgg gag ggt ctg atc gac ggc tgg tac ggc ttc agg cac cag aac gcc     1104
Trp Glu Gly Leu Ile Asp Gly Trp Tyr Gly Phe Arg His Gln Asn Ala
        355                 360                 365

cag ggt gag ggc act gct gct gac tac aag agc acc cag tcc gcc atc     1152
Gln Gly Glu Gly Thr Ala Ala Asp Tyr Lys Ser Thr Gln Ser Ala Ile
    370                 375                 380

gac cag atc acc ggt aag ctg aac cgt ctc atc gag aag act aac cag     1200
Asp Gln Ile Thr Gly Lys Leu Asn Arg Leu Ile Glu Lys Thr Asn Gln
385                 390                 395                 400

cag ttc gag ctc atc gac aac gag ttc act gag gtc gag aag cag atc     1248
Gln Phe Glu Leu Ile Asp Asn Glu Phe Thr Glu Val Glu Lys Gln Ile
                405                 410                 415

ggc aac gtg atc aac tgg acc agg gac tcc atg act gag gtg tgg tcc     1296
Gly Asn Val Ile Asn Trp Thr Arg Asp Ser Met Thr Glu Val Trp Ser
            420                 425                 430

tac aac gct gag ctc ctc gtc gcc atg gag aac cag cac acc atc gac     1344
Tyr Asn Ala Glu Leu Leu Val Ala Met Glu Asn Gln His Thr Ile Asp
        435                 440                 445

ctg gct gac tcc gag atg aac aag ctc tac gag cgt gtg agg agg cag     1392
Leu Ala Asp Ser Glu Met Asn Lys Leu Tyr Glu Arg Val Arg Arg Gln
    450                 455                 460

ctg cgc gag aac gct gag gag gac ggt act ggt tgc ttc gag atc ttc     1440
Leu Arg Glu Asn Ala Glu Glu Asp Gly Thr Gly Cys Phe Glu Ile Phe
465                 470                 475                 480

cac aag tgc gac gac gac tgc atg gcc tcc atc cgt aac aac acc tac     1488
His Lys Cys Asp Asp Asp Cys Met Ala Ser Ile Arg Asn Asn Thr Tyr
                485                 490                 495

gac cac agc aag tac agg gag gag gcc atg cag aac agg atc cag atc     1536
Asp His Ser Lys Tyr Arg Glu Glu Ala Met Gln Asn Arg Ile Gln Ile
            500                 505                 510
```

```
gac ccc gtc aag ctg agc agc ggc tac aag gac gtg atc ctg tgg ttc     1584
Asp Pro Val Lys Leu Ser Ser Gly Tyr Lys Asp Val Ile Leu Trp Phe
        515                 520                 525

agc ttc ggc gct tcc tgc ttc atc ctc ctg gcc atc gcc atg ggc ctg     1632
Ser Phe Gly Ala Ser Cys Phe Ile Leu Leu Ala Ile Ala Met Gly Leu
    530                 535                 540

gtc ttc atc tgc gtg aag aac ggt aac atg agg tgc act atc tgc atc     1680
Val Phe Ile Cys Val Lys Asn Gly Asn Met Arg Cys Thr Ile Cys Ile
545                 550                 555                 560

taa                                                                 1683


<210> SEQ ID NO 6
<211> LENGTH: 560
<212> TYPE: PRT
<213> ORGANISM: Artificial Sequence
<220> FEATURE:
<223> OTHER INFORMATION: Synthetic Construct

<400> SEQUENCE: 6

Met Asn Thr Gln Ile Leu Val Phe Ala Leu Val Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Ser Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Ile Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Ile Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285
```

```
Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Met Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Arg Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Ala Met Gly Leu
    530                 535                 540

Val Phe Ile Cys Val Lys Asn Gly Asn Met Arg Cys Thr Ile Cys Ile
545                 550                 555                 560


<210> SEQ ID NO 7
<211> LENGTH: 9792
<212> TYPE: DNA
<213> ORGANISM: Artificial Sequence
<220> FEATURE:
<223> OTHER INFORMATION: EcoR-EcoR1 insert HVP310
<220> FEATURE:
<221> NAME/KEY: misc_feature
<222> LOCATION: (1)..(3661)
<223> OTHER INFORMATION: HVT Upstream Us2 area
<220> FEATURE:
<221> NAME/KEY: misc_feature
<222> LOCATION: (3683)..(4357)
<223> OTHER INFORMATION: PRV gB promoter, extended
<220> FEATURE:
<221> NAME/KEY: misc_feature
<222> LOCATION: (4361)..(6096)
<223> OTHER INFORMATION: Codon optimised H5 HA gene
<220> FEATURE:
<221> NAME/KEY: misc_feature
<222> LOCATION: (6139)..(9787)
<223> OTHER INFORMATION: HVT Us2 downstream area

<400> SEQUENCE: 7

gaattccaga ctaaatgccc cggcccaatt tgtcaagtgt gcagtcacgg aggcgtcgac     60
```

-continued

```
cgtgtccccg gcattaaaca ggaaagcgtt aaagtttttg aatgttaggt cacaggtaca    120
aacataaatg tttgtacaaa caggtaacag gtacaaacat aaatgccccg gcataaatgt    180
cccttacggc ggatcgaaac gacattaggc atactcgggt accattttgc attccgatca    240
gcacggatga aattaggcag gaatgcggtt tatattatgc ggcattggac aaacgatatg    300
gcattgattg gcagtttatg aatgtcttca tgttgggcgt aaacggattc ctattggttc    360
agaagacaac gacgatatat ttagagagaa aaagctaccc agcataggat aaacacacat    420
tgagcattga gagacatagg tatcggtatg gatgggaaaa ctacacacgt gaacaccaaa    480
cgacttatat actcgagcgg tgatactact gagcaagaat gcactgcatc tgagccactg    540
aatgaagact gtgatgaaaa tgtgaccatc gatggaattg gagaagaata tgcgcagttc    600
ttcatgtccc cgcaatgggt cccaaatcta catcgcttga gcgaggatac caaaaaggta    660
taccgatgta tggtttccaa cagactcaat tattttccct attatgaggc gttcaggcgg    720
tctttgtttg atatgtatat gctaggtcgg ttggggcgtc gacttaagcg atctgactgg    780
gagactatta tgcatctgtc accaacgcaa agtcggcgtc tacatagaac tttaagattt    840
gtggagcgta gaattatccc atctaacagt tatatacgca catcgggcca cgttccgcct    900
tcgagggcac ttccgacaga tacgaattta aagatggatg aataattaaa ttggaaagag    960
taactacatt aatcgagcgt catgacggcg tcccgtgaaa atgggaattt tctactcgaa   1020
acaccgtgac atttgacaga cctggaattg ttattctgat atatagtggg tgtgtctggc   1080
cggcaacata cataatgtgc atgcgaaacc actttttcag tgtacgctga cattgtgcaa   1140
cacggagggg tagcatctac atacaatata tgttgattaa tgattggaga aaaaactatg   1200
cagctcgccg atcatatggc taactcgcct tcgtctatat ggcggacccc gcgggaaaaa   1260
tcgacgtacc atctgattta caacaccagt aatgaacatg tcgcatccct gcccagatct   1320
gtgcgcccat tggcgcggat cgttgtgaat gccgccgaaa cacttcaggt cggtatgaga   1380
gccgggaggc cgccatcagc aggagtttgg cgagaggtgt ttgatagaat gatgacagcc   1440
ttccgtgacc acgagcctac tgcgacattt aatgctgcaa atcccattag aaaaatggtc   1500
gagacagttc tacagaataa tgaagagccc ccgcggacgc atgctgaaat gggtaatcgc   1560
cttatgaaca ttatgtactg gtgttgcttg ggacacgcag gacaatgctc gatatggcag   1620
ttgtacgaga cgaatcaggc cattttaagt ttattagatg aagtggttat cggcacaaca   1680
aatccctttt gcaccctcga gcaatactgg aagccattat gcaccgcaat cgccaacaag   1740
gggacctcat cgcttgttga ggatgccaaa gtggccgagt acctggttag catgcgcaaa   1800
ttgatataac ataggcacgc tctgatgtta cagaccacaa taccgcatac atttattgta   1860
aggttgttaa taaaggttta ttctatgtaa gactacaata ctttcgacat tgcttgtata   1920
catattaaat actttctcaa gttcctatta cataaaatgg gatctatcat tacattcgtt   1980
aagagtctgg ataattttac tgtttgccag cttcgatctt ggaacgtact gtggatagtg   2040
ccttacttgg aatcgtgaaa atttgaaacg tccattattt ggatatcttc cggttgtccc   2100
atatcccgcc ctggtaccgc tcggatacct tgcccgtatg gattcgtatt gacagtcgcg   2160
caatcgggga ccaacaacgc gtgggtccac actcattcgg aaattttccg atgattctga   2220
atatttattg ccgctcgtta cgagtcgttg gacatatctg taatacattt cttcttctga   2280
aggatcgctg cacatttgat ctatacattg gccaggatgt tcaagtctca gatgttgcat   2340
tctggcacag cacaacttta tggcatttcc gatgtaatcg tccggcagcc ctgggggagt   2400
tctatattcg catattggga tggtaaggac aatagcagat ctcgcaacct ccagggaggc   2460
```

-continued

```
tataataacg tttttaaagg atggatttct cataaaaatc tgtcgcaaat tacactgaga   2520
atatccttta ctagcgccga ttgagagcat cgtcgtccaa ttttctaaat ggaaagaaaa   2580
caaggcgggc aagagtgttc caaacatttt catttcggc gaatctctca aatcccatgg   2640
cgtgcaattg attgcaaaat tggcacttcc gttcacgttt gtatctccaa actctaagac   2700
acttttaatt gaaaaactac gttctagtgt ggaaagaaac ctataggcag accatagaac   2760
tatttgacac cacatatctt tttgtatgtc aaactgacca tgatcgtatg ttgctgaatg   2820
cactagggca attcgctcgc gcgactccat acattgaata attccacacg tcagctcatc   2880
ggttagcaag gtccagtagt tgaagtcatt tatttttccc cgcggctggc caaatctacc   2940
tctgggaata tccaagttgt cgaatatgat cgcaccggct ctggtcatgg tgaaggaact   3000
gtagcataaa gacgcaggta tcataggggt aatatttttt tattcactca catactaaaa   3060
gtaacgcata ttagcaccat gtatgggcta tcaattgaca tttgcgtagc actacatcac   3120
gattatgtac aacataatgg gacaacatat ggcaagtaga tgcaatttcc tcacactagt   3180
tgggtttatc tactattgaa ttttccccta tctgtgatac acttgggagc ctctacaagc   3240
atattgccat catgtacgtt tttatctact gtcttaacgc ccatgggaac ggaggcgtcg   3300
tcgtcatgta ttggacggca acataggcag caacacaaat tgcgtttagg tggggtgcat   3360
gtggactcga taccaagccc ctgcagctgg ggaacgtctg gtggagagcc gataatttga   3420
tatacgcacg ccatattact gtcgttgaag tacgccttat cttctatgtt ttcaaattta   3480
ggttcccaag tggacgtgag aagtgtttgt atctcacatg gaatggccca aggcattcca   3540
gcccaggtgc ctggtacttt aatggcaaac aaacgttttg gtagaggtat tgattctatt   3600
gcagttctgc agatatctgc agccccgagt atccacaggc tatacgatac gttatcggag   3660
gcaagcttgg cgcgccggat ctcgctgctg cacacgtacg tggcggtggc cgccgggttc   3720
cgcgcacggc gcgcgttctg cgaggccgcc gcgcgcgcgg gcaccgtcgt ggacgagcgc   3780
gagacgggct gcttcgacgc gcacagcttc atgaaggcca cggtgcagcg ccaccccgtg   3840
gacgccgcgc tcctcccggc gctcacgcac aagttcttcg agctcgtcaa cgggccgctc   3900
ttcgcgcacg acacgcacgc cttcgcccag tcccccaaca cggcgctcta ctttgcggtg   3960
gagaacgtgg gcctcctgcc gcacctgaag gaggagctgg cgcgcttcat ggtggcccgc   4020
gattggtgcg tcagtgagtt ccgcggcttc taccgcttcc agacggccgg cgtaaccgcc   4080
acccagcggc aggcctggcg atatatccgc gagctggtgc tggcggttgc agtcttcagg   4140
tccgtcttcc actgcgggga cgtcgaggtc ctccgcgcgg atcgcttcgc cggacgcgac   4200
gggctgtacc tgacctacga ggcgtcttgc cccgctggtg gcggtctttg gcgcgggccc   4260
cgcgggcatc ggcccgggca ccacggcggt gctggcctcg gacgtctttg gcctgctcca   4320
caccacgctg ctgctgcgcg gggcgccgtc gcgctagaga tccaagatat caaagccatg   4380
gagaagatcg tcctcctgct ggctatcgtc tccctggtca agagcgacca gatctgcatc   4440
ggctaccacg ccaacaactc taccgagcag gtggacacca tcatggagaa gaacgtgacc   4500
gtcactcacg cccaggacat cctcgagaag actcacaacg gaaagctctg cgacctcgac   4560
ggcgtcaagc ctctgatcct gcgtgactgc tccgtggctg gttggctcct gggcaacccc   4620
atgtgcgacg agttcctcaa cgtgcccgag tggtcctaca tcgtcgagaa gatcaacccc   4680
gccaacgacc tgtgctaccc tggcaacttc aacgactacg aggagctcaa gcacctgctc   4740
tcccgtatca accacttcga gaagatccag atcatcccca agtcctcctg gtccgaccac   4800
```

-continued

```
gaggcttcta gcggtgtgtc cagcgcttgc ccctaccagg gccgctccag cttcttccgc   4860
aacgtcgtgt ggctgatcaa gaaggacaac gcttacccaa ctatcaagcg cagctacaac   4920
aacactaacc aggaggacct gctggtgctg tggggcatcc accaccctaa cgacgccgct   4980
gagcagactc gtctctacca gaaccctact agctacatct ccgtgggaac ctctaccctg   5040
aaccagaggc tggtgcccaa gatcgctacc aggtccaagg tcaacggtca gtctggtagg   5100
atggagttct tctggactat cctgaagccc aacgacgcta tcaacttcga gtctaacggt   5160
aacttcatcg ctcctgagaa cgcctacaag atcgtcaaga agggtgactc tactatcatg   5220
aagtctgagc tggagtacgg taactgcaac accaagtgcc agacccctat cggtgccatc   5280
aactcctcta tgcctttcca caacatccac cccctgacca tcggtgagtg ccctaagtac   5340
gtcaagtcta accgtctggt cctggctact ggactgcgta actctcccca gggtgagcgc   5400
cgtcgtaaga agaggggcct cttcggtgcc atcgctggct tcatcgaggg tggatggcag   5460
ggcatggtgg acggctggta cggttaccac cacagcaacg agcagggctc cggttacgct   5520
gccgacaagg agtctaccca gaaggctatc gacggcgtca ccaacaaggt gaactccatc   5580
atcgacaaga tgaacaccca gttcgaggct gtgggcaggg agttcaacaa cctggagcgt   5640
cgtatcgaga acctgaacaa gaagatggag gacggtttcc tggacgtctg gacttacaac   5700
gccgagctcc tggtgctgat ggagaacgag cgcaccctgg acttccacga ctccaacgtg   5760
aagaacctct acgacaaggt ccgcctccag ctccgcgaca acgctaagga gctgggtaac   5820
ggttgcttcg agttctacca caggtgcgac aacgagtgca tggagtccgt gcgtaacggc   5880
acctacgact acccccagta ctccgaggag gcccgtctca agagggagga gatctccggt   5940
gtgcgcctgg agagcatcgg tacttaccag atcctctcca tctactccac cgtcgccagc   6000
tccctcgccc tggctatcat ggtggctggc ctctccctgt ggatgtgctc caacggcagc   6060
ctgcagtgca agatctgcat ctaactggat atcaaggatc tctcgaggat atcctgcagg   6120
tcgactctag gaagcttgcc tccgattcta gcattacata gccggtcagt agatcctgcc   6180
attcggtagc gcaaccggct acatcttcaa acagtctcac gataaatgca tctctcgttc   6240
ctgccaatcc ggaaccgggc ataccactcc cgcctgccga tttaattctc acaattgggc   6300
gatgccggcg gggcaaaacg aatgtggatt tggcaaaccg acacaggtct gctgtacgga   6360
ctaatatggg cacacccaca tcattcttca gatgctccat gcattgttct atgagaaaga   6420
tccatagggt ggaggcagcg tcacgagatc gcccaggcaa tcgatcgcat tcgtctagta   6480
aagtgacgag agttatcatg cacacaccca tgcccacgcc ttccgaataa ctggagctgt   6540
ggaagatcgg aaacgtcttt ttgactgccg gtctcgtact actttcgcac aggtgtatac   6600
ccggacgcgt actatatatt ttatatcatc caacgtccga aattacatac gtggcggcga   6660
tggaagtaga tgttgagtct tcgaaagtaa gtgcctcgaa tatgggtatt gtctgtgaaa   6720
atatcgaaag cggtacgacg gttgcagaac cgtcgatgtc gccagatact agtaacaata   6780
gcttcgataa cgaagacttc cgtgggcctg aatacgatgt ggagataaat accagaaaat   6840
ctgctaatct tgatcgtatg gaatcttcgt gccgtgaaca acgagcggcg tgcgaacttc   6900
gaaagtgttc gtgtcctacg tctgccgtgc gcatgcaata cagtattctt tcatctctcg   6960
ctccgggttc agagggtcat gtatatatat gtactagata cggggacgcg gaccaaaaaa   7020
aatgcatagt gaaggcagtc gttggaggaa agaatcccgg gagggaagtg gatattttaa   7080
aaaccatctc acataaatca attataaaat taatccatgc ctataaatgg aaaaatgttg   7140
tgtgtatggc aatgcgtgta tatcgttatg atcttttcac atatattgac ggagtcggcc   7200
```

```
ctatgcccct tcaacagatg atctatattc aacgtggact actagaggcg ctagcataca   7260
tacatgaaag gggcatcatt caccgagacg taaagacgga gaatatattc ttggataatc   7320
acgaaaatgc agttttgggt gacttcggtg ctgcatgcca actaggagat tgtatagata   7380
cgccccaatg ttacggttgg agcggaactg tggaaacaaa ttcgccggaa ttatctgcac   7440
ttgatccgta ttgcacaaaa acagatattt ggagtgccgg attggttcta tatgagatgg   7500
caattaaaaa tgtaccattg tttagtaagc aggtgaaaag ttcgggatct cagctgagat   7560
ccataatacg gtgcatgcaa gtgcatgaac tggagtttcc ccgcaacgat tctaccaacc   7620
tctgtaaaca tttcaaacaa tatgcggttc gtgtacgacc gccttatacc attcctcgag   7680
ttataagaaa tgggggatg ccaatggatg ttgaatatgt catttctaaa atgcttacgt   7740
ttgaccagga gttcagacct tctgctaagg aaatattgaa tatgccccta tttactaagg   7800
cgccgattaa cctgcttaat atcacaccct ctgacagtgt ctaacggtat acaggcggga   7860
gcgggtcgtg gcgtcatcat caccacttga gaatttatat tttgaattgt tgattgataa   7920
attaacctga ttcattgaga actgaaacgc catattggtt tcttggatat gtctacaaca   7980
attagttaaa ttgctatgtt ctactgcgag taacatttga taagttgtaa gagacgggcg   8040
actcatgtcg aagttgacga atataaagta cataacgtgt ttagaatacc cagaatccga   8100
atagtccgcg gggcgtctt ctcgcgtgag taccaaatac tgagttgaac ttgaaaatgc   8160
taaatctgtg acactctttg tgtgatgatt attgtcacca cttcgaagat ggcttcgaca   8220
ttcatgatgt tctggtgttt gtttggaatc gtaatagcgc ttgtttcgtc caagtctgac   8280
aacaaagaaa atctgaagaa ttatatcacg gataagtcaa ccaatattag aatacccacg   8340
ccattatttg tatcaacgga aaactcttat cccacaaaac atgtaatcta cgatgaaaac   8400
tgtggcttcg ctgtactcaa tcctataagt gaccccaaat atgtcctttt gagccagctt   8460
ctaatgggaa ggcgcaaata tgatgcgacg gtcgcgtggt ttgttctcgg taaaatgtgt   8520
gccagattaa tatatttgcg cgaattttat aactgctcga caaatgagcc ttttggcaca   8580
tgttctatga gctctcctgg atggtgggac aggcgctacg tctcaaccag tttcatttct   8640
cgcgacgaat tacagctggt ttttgcagcg ccgtcccgag aattagatgg tttatatacg   8700
cgcgtagtag ttgtcaacgg ggactttact acggccgata taatgtttaa tgttaaagtg   8760
gcatgtgcct tttcaaagac tggaatagaa gatgatacat tatgcaaacc ctttcatttc   8820
tttgccaatg caacattgca caatttaacc atgattagat cggtaactct tcgagcgcac   8880
gaaagccatt taaaggaatg ggtggcacgg agaggtggta acgtccctgc agtgctactt   8940
gagtctacca tgtatcatgc atccaatctg cctagaaatt tcagggattt ctacataaag   9000
tctccagatg attataagta taatcaccta gatgggccat ctgtaatgct catcactgac   9060
agacctagtg aagatttgga tgggaggctc gttcaccaaa gtgacatttt tactactaca   9120
agtcctataa aacaggtccg gtatgaagag catcagtcac atacaaagca gtatcctgta   9180
aacaaaatac aagctataat ttttttgata gggttaggct cgttcattgg aagcatattc   9240
gtagttttgg tagtatggat tatacgcaga tattgcaatg gagcgcggag tgggggaacg   9300
ccccccagtc ctcgccggta tgtgtatacc aggctatgat cacgtgtgaa acttgggcgg   9360
acctgtatca tatgtacacc gtccctattc gtttatagcc agtacgtgtt atctgcacat   9420
agaggaacat gtgtcatact gggatcgcat gcatggtatg tgtgactcta atattattct   9480
gtatcataat aaaaacacag tgcatggtat atagaggatc gctggtaagc actacggtag   9540
```

-continued

```
accaatcggc tcagattgca ttctttggca tcgataccgt tgttaattta tatggcaaag   9600

tcttgttcat gggagatcag tatttggagg aaatatactc tggaacgatg gaaatactca   9660

aatggaatca agctaaccgc tgctattcta ttgcgcatgc aacatattac gccgactgtc   9720

ctataatcag ttctacggta ttcagaggat gccgggacgc cgttgtttat actaggcccc   9780

acagcagaat tc                                                       9792
```